US011878077B2

(12) United States Patent
Sivik et al.

(10) Patent No.: US 11,878,077 B2
(45) Date of Patent: Jan. 23, 2024

(54) FIBROUS WATER-SOLUBLE UNIT DOSE ARTICLES COMPRISING WATER-SOLUBLE FIBROUS STRUCTURES

(71) Applicant: The Procter & Gamble Company, Cincinnati, OH (US)

(72) Inventors: Mark Robert Sivik, Mason, OH (US); Frank William Denome, Cincinnati, OH (US); Mark William Hamersky, Hamilton, OH (US); Sarah Ann Delaney, Hebron, KY (US); Sol Melissa Escobar, Mason, OH (US); Jack Wesley English, III, Liberty Township, OH (US); Min Mao, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 362 days.

(21) Appl. No.: 16/823,375

(22) Filed: Mar. 19, 2020

(65) Prior Publication Data
US 2020/0297645 A1 Sep. 24, 2020

(30) Foreign Application Priority Data

Mar. 19, 2019 (EP) ..................................... 19163586

(51) Int. Cl.
*A61K 9/28* (2006.01)
*A61K 9/20* (2006.01)

(52) U.S. Cl.
CPC ............ *A61K 9/282* (2013.01); *A61K 9/2059* (2013.01)

(58) Field of Classification Search
CPC .............................. A61K 9/282; A61K 9/2059
See application file for complete search history.

(56) References Cited

U.S. PATENT DOCUMENTS

| | | |
|---|---|---|
| 3,293,718 A | 12/1966 | Sheets |
| 3,859,125 A | 1/1975 | Miller et al. |
| 4,180,558 A | 12/1979 | Goldberg et al. |
| 4,286,016 A | 8/1981 | Dimond et al. |
| 4,287,219 A | 9/1981 | Fabre |
| 4,315,965 A | 2/1982 | Mason et al. |
| 4,342,813 A | 8/1982 | Erickson |
| 4,349,531 A | 9/1982 | Mlodozeniec et al. |
| 4,377,615 A | 3/1983 | Suzuki et al. |
| 4,397,391 A | 8/1983 | Cornelissens |
| 4,415,617 A | 11/1983 | D'Elia |
| 4,639,390 A | 1/1987 | Shoji |
| 4,892,758 A | 1/1990 | Serbiak et al. |
| 4,923,660 A | 5/1990 | Willenberg et al. |
| 5,041,252 A | 8/1991 | Fujii et al. |
| 5,110,678 A | 5/1992 | Narukawa et al. |
| 5,120,888 A | 6/1992 | Nohr et al. |
| 5,135,804 A | 8/1992 | Harpell et al. |
| 5,158,810 A | 10/1992 | Oishi et al. |
| 5,208,104 A | 5/1993 | Ueda et al. |
| 5,230,853 A | 7/1993 | Colegrove et al. |
| 5,246,603 A | 9/1993 | Tsaur |
| 5,342,335 A | 8/1994 | Rhim |
| 5,362,532 A | 11/1994 | Famili et al. |
| 5,364,627 A | 11/1994 | Song |
| 5,387,147 A | 2/1995 | Ohshima et al. |
| 5,429,874 A | 7/1995 | Vanputte |
| 5,455,114 A | 10/1995 | Ohmory et al. |
| 5,470,424 A | 11/1995 | Isaac et al. |
| 5,470,653 A | 11/1995 | Honeycutt et al. |
| 5,486,418 A | 1/1996 | Ohmory et al. |
| 5,518,730 A | 5/1996 | Fuisz |
| 5,520,924 A | 5/1996 | Chapman et al. |
| 5,538,735 A | 7/1996 | Ahn |
| 5,585,059 A | 12/1996 | Kobayashi et al. |
| 5,651,987 A | 7/1997 | Fuisz |
| 5,691,015 A | 11/1997 | Tsukamoto et al. |
| 5,705,183 A | 1/1998 | Phillips et al. |
| 5,716,692 A | 2/1998 | Warner et al. |
| 5,717,026 A | 2/1998 | Ikimine et al. |
| 5,735,812 A | 4/1998 | Hardy |
| 5,780,418 A | 7/1998 | Niinaka et al. |
| 5,827,586 A | 10/1998 | Yamashita et al. |
| 5,840,423 A | 11/1998 | Sano et al. |
| 5,863,887 A | 1/1999 | Gillette |
| 5,879,493 A | 3/1999 | Johnson et al. |
| 5,911,224 A | 6/1999 | Berger |
| 5,914,124 A | 6/1999 | Mahoney et al. |
| 5,942,179 A | 8/1999 | Tallentire et al. |
| 5,972,869 A | 10/1999 | Cao |
| 6,008,181 A | 12/1999 | Cripe |
| 6,037,319 A | 3/2000 | Dickler et al. |
| 6,066,396 A | 5/2000 | Inada et al. |
| 6,080,346 A | 6/2000 | Jack |
| 6,130,193 A | 10/2000 | Gillette |
| 6,175,054 B1 | 1/2001 | Jacques |
| 6,197,238 B1 | 3/2001 | Wang et al. |
| 6,207,274 B1 | 3/2001 | Ferenc et al. |
| 6,274,162 B1 | 8/2001 | Steffenino et al. |
| 6,319,510 B1 | 11/2001 | Yates |
| 6,406,797 B1 | 6/2002 | Vanputte |
| 6,420,625 B1 | 7/2002 | Jones et al. |
| 6,448,462 B2 | 9/2002 | Groitzsch et al. |
| 6,465,407 B2 | 10/2002 | Hayashi et al. |
| 6,552,123 B1 | 4/2003 | Katayama et al. |
| 6,576,575 B2 | 6/2003 | Griesbach, III et al. |
| 6,608,121 B2 | 8/2003 | Isozaki et al. |
| 6,657,004 B2 | 12/2003 | Mizutani |
| 6,699,826 B1 | 3/2004 | Saijo et al. |
| 6,727,215 B2 | 4/2004 | Roberts |
| 6,730,648 B2 | 5/2004 | Gorlin et al. |
| 6,783,852 B2 | 8/2004 | Inada et al. |
| 6,787,512 B1 | 9/2004 | Verrall et al. |
| 6,808,598 B1 | 10/2004 | Takeuchi et al. |
| 6,818,606 B1 | 11/2004 | Hanada et al. |
| 6,825,158 B2 | 11/2004 | Mitra et al. |

(Continued)

FOREIGN PATENT DOCUMENTS

AU 2004/202461 B2 11/2007
CA 2695068 A1 9/2010

(Continued)

OTHER PUBLICATIONS

PCT Search Report for appl. No. PCT/US2018/015354, dated May 14, 2018, 13 pages.

(Continued)

*Primary Examiner* — Shirley V Gembeh

(57) ABSTRACT

Described herein is a fibrous water-soluble unit dose with an active agent in the form of an acid.

13 Claims, 7 Drawing Sheets

(56) References Cited

U.S. PATENT DOCUMENTS

| | | |
|---|---|---|
| 6,898,921 B2 | 5/2005 | Duffield |
| 6,949,498 B2 | 9/2005 | Murphy et al. |
| 6,956,070 B2 | 10/2005 | Fujiwara et al. |
| 6,977,116 B2 | 12/2005 | Cabell et al. |
| 7,026,049 B2 | 4/2006 | Endo et al. |
| 7,041,628 B2 | 5/2006 | Sunder |
| 7,067,575 B2 | 6/2006 | Kitamura et al. |
| 7,083,047 B2 | 8/2006 | Bone et al. |
| 7,094,744 B1 | 8/2006 | Kobayashi et al. |
| 7,115,551 B2 | 10/2006 | Hasenorhrl et al. |
| 7,169,740 B2 | 1/2007 | Sommerville-Roberts et al. |
| 7,196,026 B2 | 3/2007 | Di Luccio et al. |
| RE39,557 E | 4/2007 | Moe |
| 7,226,899 B2 | 6/2007 | Cole et al. |
| 7,285,520 B2 | 10/2007 | Krzysik et al. |
| 7,387,787 B2 | 6/2008 | Fox |
| 7,407,669 B2 | 8/2008 | Leung et al. |
| 7,429,273 B2 | 9/2008 | DeDominicis et al. |
| 7,445,643 B2 | 11/2008 | Sadlowski |
| 7,446,084 B2 | 11/2008 | Barthel et al. |
| 7,491,407 B2 | 2/2009 | Pourdeyhimi et al. |
| 7,507,698 B2 | 3/2009 | Franzolin et al. |
| 7,547,737 B2 | 6/2009 | Kochvar et al. |
| 7,563,757 B2 | 7/2009 | Kouvroukoglou et al. |
| 7,708,840 B2 | 5/2010 | Wiedemann et al. |
| 7,727,946 B2 | 6/2010 | Catalfamo et al. |
| 7,824,588 B2 | 11/2010 | Yang et al. |
| 7,856,989 B2 | 12/2010 | Karles et al. |
| 7,967,801 B2 | 6/2011 | Hammons et al. |
| 8,080,511 B2 | 12/2011 | Dreyer |
| 8,338,358 B2 | 12/2012 | Bernhardt |
| 8,349,232 B2 | 1/2013 | Pourdeyhimi et al. |
| 8,785,361 B2 | 7/2014 | Sivik |
| 9,068,151 B2 | 6/2015 | Gerke et al. |
| 9,074,305 B2 | 7/2015 | Glenn, Jr. |
| 9,163,205 B2 | 10/2015 | Sivik |
| 9,175,250 B2 | 11/2015 | Sivik |
| 9,259,132 B2 | 2/2016 | Sumnicht et al. |
| 9,267,095 B2 | 2/2016 | Delaney |
| 9,421,153 B2 | 8/2016 | Sivik |
| 9,480,628 B2 | 11/2016 | Sivik |
| 9,493,726 B2 | 11/2016 | Vinson |
| 9,506,022 B2 | 11/2016 | Ronco et al. |
| 9,796,948 B2 | 10/2017 | Shearouse |
| 9,926,520 B2 | 3/2018 | Panandiker et al. |
| 10,045,915 B2 | 8/2018 | Glenn, Jr. |
| 2001/0037851 A1 | 11/2001 | Mortellite et al. |
| 2002/0013251 A1 | 1/2002 | Hayashi |
| 2002/0018906 A1 | 2/2002 | Clark |
| 2002/0098994 A1 | 7/2002 | Zafar |
| 2002/0161088 A1 | 10/2002 | Kochvar et al. |
| 2002/0173213 A1 | 11/2002 | Chu et al. |
| 2003/0017208 A1 | 1/2003 | Ignatious et al. |
| 2003/0045446 A1 | 3/2003 | Dihora et al. |
| 2003/0166495 A1 | 9/2003 | Wang et al. |
| 2003/0185872 A1 | 10/2003 | Kochinke |
| 2003/0216098 A1 | 11/2003 | Carlyle |
| 2003/0224959 A1 | 12/2003 | Smith |
| 2004/0129032 A1 | 7/2004 | Severns |
| 2004/0167256 A1 | 8/2004 | Verrall et al. |
| 2004/0170836 A1 | 9/2004 | Bond et al. |
| 2004/0180597 A1 | 9/2004 | Kamada et al. |
| 2004/0204543 A1 | 10/2004 | Yang |
| 2004/0253434 A1 | 12/2004 | Patel |
| 2005/0003048 A1 | 1/2005 | Pearce et al. |
| 2005/0003980 A1 | 1/2005 | Baker |
| 2005/0003991 A1 | 1/2005 | MacQuarrie |
| 2005/0008776 A1 | 1/2005 | Chhabra et al. |
| 2005/0010010 A1 | 1/2005 | Kitamura et al. |
| 2005/0124521 A1 | 6/2005 | Sadlowski |
| 2005/0136112 A1 | 6/2005 | Gonzales et al. |
| 2005/0136780 A1 | 6/2005 | Clark et al. |
| 2005/0186256 A1 | 8/2005 | Dihel et al. |
| 2005/0209574 A1 | 9/2005 | Boehringer et al. |
| 2005/0281757 A1 | 12/2005 | Ibrahim et al. |
| 2006/0013869 A1 | 1/2006 | Ignatious et al. |
| 2006/0035042 A1 | 2/2006 | Morken |
| 2006/0083784 A1 | 4/2006 | Ignatious et al. |
| 2006/0111261 A1 | 5/2006 | Sadlowski |
| 2006/0122088 A1 | 6/2006 | Sadlowski |
| 2006/0127458 A1 | 6/2006 | Kiser et al. |
| 2006/0134412 A1 | 6/2006 | Mackey et al. |
| 2006/0160453 A1 | 7/2006 | Suh |
| 2006/0189772 A1 | 8/2006 | Scheibel et al. |
| 2006/0205628 A1 | 9/2006 | Deinhammer |
| 2006/0254013 A1 | 11/2006 | Konishi et al. |
| 2006/0254014 A1 | 11/2006 | Konishi et al. |
| 2006/0258251 A1 | 11/2006 | Konishi et al. |
| 2006/0264130 A1 | 11/2006 | Karles et al. |
| 2007/0048839 A1 | 3/2007 | Breves et al. |
| 2007/0054579 A1 | 3/2007 | Baker et al. |
| 2007/0110792 A9 | 5/2007 | Simon |
| 2007/0128256 A1 | 6/2007 | Aubrun-Sonneville |
| 2007/0134304 A1 | 6/2007 | Aubrun-Sonneville et al. |
| 2007/0134481 A1 | 6/2007 | Aubrun-Sonneville |
| 2007/0253926 A1 | 11/2007 | Tadrowski et al. |
| 2007/0259170 A1 | 11/2007 | Brown et al. |
| 2007/0259996 A1 | 11/2007 | Vicari et al. |
| 2007/0298064 A1 | 12/2007 | Koslow |
| 2008/0035174 A1 | 2/2008 | Aubrun-Sonneville et al. |
| 2008/0045431 A1 | 2/2008 | Corradini |
| 2008/0108748 A1 | 5/2008 | Buckley et al. |
| 2008/0118727 A1 | 5/2008 | Andersen |
| 2008/0146481 A1 | 6/2008 | Brown et al. |
| 2008/0149119 A1 | 6/2008 | Marquez et al. |
| 2008/0220054 A1 | 9/2008 | Shastri et al. |
| 2008/0226919 A1 | 9/2008 | Hosoda et al. |
| 2008/0242572 A1 | 10/2008 | Icht et al. |
| 2008/0269095 A1 | 10/2008 | Aubrun-Sonneville |
| 2009/0004254 A1 | 1/2009 | Maibach |
| 2009/0041820 A1 | 2/2009 | Wu et al. |
| 2009/0061496 A1 | 3/2009 | Kuhn et al. |
| 2009/0061719 A1 | 3/2009 | Shibutani et al. |
| 2009/0155326 A1 | 6/2009 | Mack et al. |
| 2009/0181587 A1 | 7/2009 | Kang et al. |
| 2009/0249558 A1 | 10/2009 | Fileccia et al. |
| 2009/0285718 A1 | 11/2009 | Privitera et al. |
| 2009/0291282 A1 | 11/2009 | Kitamura et al. |
| 2010/0018641 A1 | 1/2010 | Branham et al. |
| 2010/0021517 A1 | 1/2010 | Ahlers et al. |
| 2010/0105821 A1 | 4/2010 | Verrall et al. |
| 2010/0166854 A1 | 7/2010 | Michniak-Kohn et al. |
| 2010/0196440 A1 | 8/2010 | Stark et al. |
| 2010/0266668 A1 | 10/2010 | Coffee et al. |
| 2010/0279905 A1 | 11/2010 | Glenn, Jr. et al. |
| 2010/0285101 A1 | 11/2010 | Moore et al. |
| 2011/0136719 A1 | 6/2011 | Jalbert et al. |
| 2011/0159267 A1 | 6/2011 | Lee et al. |
| 2011/0223381 A1 | 9/2011 | Mackey et al. |
| 2011/0230112 A1 | 9/2011 | Roé et al. |
| 2011/0301070 A1 | 12/2011 | Ochomogo et al. |
| 2012/0021026 A1 | 1/2012 | Glenn, Jr. et al. |
| 2012/0027838 A1 | 2/2012 | Gordon et al. |
| 2012/0048769 A1 | 3/2012 | Sivik et al. |
| 2012/0052036 A1 | 3/2012 | Glen, Jr. et al. |
| 2012/0053103 A1 | 3/2012 | Sivik et al. |
| 2012/0053108 A1 | 3/2012 | Glen, Jr. et al. |
| 2012/0058166 A1 | 3/2012 | Glen, Jr. et al. |
| 2012/0066855 A1 | 3/2012 | Schmidt et al. |
| 2012/0082037 A1 | 3/2012 | Sivik et al. |
| 2012/0154300 A1 | 6/2012 | Ma |
| 2012/0172831 A1 | 7/2012 | Darcy et al. |
| 2012/0215148 A1 | 8/2012 | Ewert et al. |
| 2012/0237576 A1 | 9/2012 | Gordon et al. |
| 2013/0171421 A1 | 7/2013 | Weisman et al. |
| 2013/0172226 A1 | 7/2013 | Dreher et al. |
| 2014/0287973 A1 | 9/2014 | Sivik et al. |
| 2014/0366294 A1 | 12/2014 | Roe |
| 2015/0048001 A1 | 2/2015 | Bailey |
| 2015/0071572 A1* | 3/2015 | Dreher .......... B65D 29/00 383/105 |
| 2015/0104856 A1 | 4/2015 | Astrid |
| 2015/0158645 A1 | 6/2015 | Meier |
| 2015/0159330 A1 | 6/2015 | Weisman et al. |

(56) References Cited

U.S. PATENT DOCUMENTS

| | | |
|---|---|---|
| 2015/0252304 A1 | 9/2015 | Souter et al. |
| 2015/0267155 A1 | 9/2015 | Brooker et al. |
| 2015/0313807 A1 | 11/2015 | Lynch |
| 2015/0329807 A1 | 11/2015 | Naqvi |
| 2015/0376550 A1 | 12/2015 | Ohtani et al. |
| 2016/0010041 A1 | 1/2016 | Sivik |
| 2016/0040105 A1 | 2/2016 | Depoot et al. |
| 2016/0101026 A1 | 4/2016 | Pratt et al. |
| 2016/0101204 A1 | 4/2016 | Lynch |
| 2016/0186095 A1 | 6/2016 | Vockenroth |
| 2016/0200501 A1 | 7/2016 | Lee |
| 2016/0258083 A1 | 9/2016 | Weisman |
| 2016/0271021 A1 | 9/2016 | Glenn, Jr. |
| 2016/0340624 A1 | 11/2016 | Sivik |
| 2016/0374906 A1 | 12/2016 | Sivik |
| 2017/0009191 A1 | 1/2017 | Maes |
| 2017/0029747 A1 | 2/2017 | Depoot et al. |
| 2017/0067002 A1 | 3/2017 | Cumming |
| 2017/0164612 A1 | 6/2017 | Ripberger |
| 2017/0226449 A1 | 8/2017 | Keuleers et al. |
| 2017/0320105 A1 | 11/2017 | Roozrokh |
| 2017/0321152 A1 | 11/2017 | Meine |
| 2017/0355938 A1 | 12/2017 | Lee |
| 2017/0368580 A1 | 12/2017 | Brandt Sanz et al. |
| 2018/0002084 A1 | 1/2018 | Keuleers et al. |
| 2018/0118906 A1 | 5/2018 | Lee et al. |
| 2018/0216050 A1 | 8/2018 | Denome |
| 2018/0216052 A1 | 8/2018 | Denome |
| 2018/0216053 A1* | 8/2018 | Denome .............. C11D 3/3723 |
| 2018/0223229 A1 | 8/2018 | Tan |
| 2018/0338890 A1 | 11/2018 | Glenn, Jr. |
| 2020/0140791 A1 | 5/2020 | Delaney |
| 2020/0299622 A1 | 9/2020 | Sivik et al. |
| 2020/0299623 A1 | 9/2020 | Sivik et al. |
| 2020/0299888 A1 | 9/2020 | Sivik et al. |

FOREIGN PATENT DOCUMENTS

| | | |
|---|---|---|
| DE | 10 2007 011606 A1 | 9/2008 |
| EP | 0376893 A2 | 7/1990 |
| EP | 0299532 B1 | 9/1992 |
| EP | 1 275 368 A1 | 1/2003 |
| EP | 1 306 425 A2 | 5/2003 |
| EP | 1 409 628 B1 | 2/2006 |
| EP | 1 512 701 B1 | 6/2006 |
| EP | 1 887 036 A2 | 2/2008 |
| EP | 1 888 036 | 2/2008 |
| EP | 1 436 376 B1 | 4/2010 |
| EP | 2 226 379 A1 | 9/2010 |
| EP | 1 948 771 B1 | 12/2010 |
| EP | 2 319 965 A1 | 5/2011 |
| EP | 2 363 432 A1 | 9/2011 |
| EP | 2 363 517 A1 | 9/2011 |
| EP | 2 395 142 A1 | 12/2011 |
| EP | 3409754 A1 | 12/2018 |
| EP | 3650523 A1 | 5/2020 |
| GB | 2107579 A | 5/1993 |
| GB | 2375542 | 11/2002 |
| GB | 2449418 | 11/2008 |
| HU | 221299 B1 | 9/2002 |
| JP | 62-156348 | 7/1987 |
| JP | 3040879 A | 2/1991 |
| JP | 3101618 A | 4/1991 |
| JP | 09279457 | 10/1997 |
| JP | 10008364 | 1/1998 |
| JP | 10158700 A | 6/1998 |
| JP | H10204499 A | 8/1998 |
| JP | 2000169896 A | 6/2000 |
| JP | 2001120650 A | 5/2001 |
| JP | 2009079329 | 4/2009 |
| KR | 20150100464 A | 9/2015 |
| WO | WO 1992/006603 A1 | 4/1992 |
| WO | WO 1994/002377 A1 | 2/1994 |
| WO | WO 94/04656 A2 | 3/1994 |
| WO | WO 95/23888 A1 | 9/1995 |
| WO | WO 99/57155 | 11/1999 |
| WO | WO 2000/013680 A2 | 3/2000 |
| WO | 0027958 A1 | 5/2000 |
| WO | WO 01/25322 A1 | 4/2001 |
| WO | WO 2001/54667 A1 | 8/2001 |
| WO | 0208380 A1 | 1/2002 |
| WO | WO 03/060007 A1 | 7/2003 |
| WO | WO 2004/009335 A1 | 1/2004 |
| WO | WO 2004/081162 A1 | 9/2004 |
| WO | 2005061685 A1 | 7/2005 |
| WO | WO 2005/068604 A1 | 7/2005 |
| WO | 2006005919 A1 | 1/2006 |
| WO | 2006059811 A1 | 6/2006 |
| WO | WO 2006/106514 A2 | 10/2006 |
| WO | WO 2007/089259 A1 | 8/2007 |
| WO | WO 2007/093558 A3 | 1/2008 |
| WO | WO 2009/022761 A1 | 2/2009 |
| WO | 2009047124 | 4/2009 |
| WO | WO 2007/014221 A3 | 4/2009 |
| WO | WO 2009/103576 A1 | 8/2009 |
| WO | WO 2009121682 * | 8/2009 |
| WO | WO 2009/121900 A1 | 10/2009 |
| WO | WO 2010/015709 A2 | 2/2010 |
| WO | WO 2011/153023 A1 | 12/2011 |
| WO | 2012003367 A3 | 3/2012 |
| WO | 2016028599 A1 | 2/2016 |
| WO | 2016119933 A1 | 8/2016 |
| WO | 2017096354 A1 | 6/2017 |
| WO | 2018140431 A1 | 8/2018 |
| WO | 2018140454 A1 | 8/2018 |
| WO | 2018140472 A1 | 8/2018 |
| WO | 2018140668 A1 | 8/2018 |
| WO | 2018140675 A1 | 8/2018 |
| WO | 2018140676 A2 | 8/2018 |
| WO | 2018231885 A1 | 12/2018 |

OTHER PUBLICATIONS

PCT Search Report for appl. No. PCT/CN2017/087707, dated Feb. 24, 2018, 12 pages.
PCT Search Report for appl. No. PCT/US2017/046391, dated Nov. 8, 2017, 17 pages.
PCT Search Report for appl. No. PCT/US2018/015357, dated Apr. 11, 2018, 14 pages.
PCT Search Report for appl. No. PCT/US2018/015358, dated Apr. 16, 2018, 15 pages.
PCT Search Report for app. No. PCT/US2019/014452, dated Apr. 8, 2019, 14 pages.
PCT Search Report for appl. No. PCT/U52019/014453, dated Apr. 8, 2019, 15 pages.
PCT Search Report for appl. No. PCT/U52019/014454, dated Apr. 5, 2019, 15 pages.
PCT Search Report for appl. No. PCT/US2019/014455, dated Apr. 5, 2019, 15 pages.
PCT Search Report for appl. No. PCT/US2019/014443, dated Apr. 17, 2019, 15 pages.
PCT Search Report for appl. No. PCT/US2019/014444, dated Apr. 16, 2019, 15 pages.
PCT Search report for appl. No. PCT/U52019/014451, dated Apr. 24, 2019, 12 pages.
PCT Search Report for appl. No. PCT/US2019/019547, dated May 22, 2019, 12 pages.
PCT Search Report for appl. No. PCT/US2019/049727, dated Jan. 2, 2020, 12 pages.
PCT Search report for appl. No. PCT/US2019/040240, dated Dec. 9, 2019, 15 pages.
PCT Search Report for appl. No. PCT/US19/40242, dated Oct. 22, 2019, 14 pages.
PCT Search Report for appl. No. PCT/US2019/052321, 12 pages, dated Dec. 12, 2019.
PCT Search Report for App. No. PCT/USS2019/060216, dated Apr. 3, 2020, 14 pages.
PCT Search Report for App. No. PCT/US2020/015189, dated May 7, 2020. 15 pgs.

(56) References Cited

OTHER PUBLICATIONS

EP Search Report for appl. No. 19163586.1-1105, dated Sep. 30, 2019, 8 pages.
PCT Search Report for appl. No. PCT/US2020/022904, dated Jun. 8, 2020, 14 pages.
Search Report for appl. No. 19163588.7-1105, dated Sep. 30, 2019, 7 pages.
PCT Search Report for appl. No. PCT/CN2017/072926, dated Feb. 6, 2017, 5 pages.
PCT Search Report for appl. No. PCT/CN2017/072927, dated Feb. 6, 2017, 6 pages.
PCT Search Report for appl. No. PCT/CN2017/072935, dated Jun. 9, 2017, 4 pages.
PCT appl. No. PCT/CN2018/074281, dated Aug. 29, 2019, 7 pages.
PCT Search Report for appl. No. PCT/ CN2018/ 074282, dated Oct. 22, 2018, 5 pages.
Makadia, et al., "Poly Lactic-co-Glycolic Acid (PLGA) as Biodegradable Controlled Drug Delivery Carrier", Polymers, 3, pp. 1377-1397 (2011).
Smith, et al., "Nanofibrous Scaffolds and Their Biological Effects", Nantechnologies for the Life Sciences, vol. 9, pp. 188-215 (2006).
Wang, et al., "A Novel Controlled Release Drug Delivery System for Multiple Drugs Based on Electrospun Nanofibers Containing Nanoparticles", Journal of Pharmaceutical Sciences, vol. 99, No. 12 (Dec. 2010).
"(E)-hept-2-enal: trans-2-heptenal", retrieved from the Internet: URL:http://www.thegoodscentscompany.com/data/rw1028241.html on Jun. 4, 2020, pp. 1/54-7/54, XP002799267.
"6-Methyl-5-hepten-2-one", retrieved from NCBIDatabase accession No. CID:9862. Jun. 6, 2020, 40 Pages, XP002799268.
"Shelf life and storage conditions of citric acid, trisodium citrate and Citrocoat N",Feb. 2017, XP002799271.
All Office Actions; U.S. Appl. No. 16/823,645.
All Office Actions; U.S. Appl. No. 16/823,656.
Jungbunzlauer2012, XP002799269.Retrieved on dated Jun. 5, 2020.
All Office Actions; U.S. Appl. No. 16/823,378, filed Mar. 19, 2020.

\* cited by examiner

FIBROUS WATER-SOLUBLE UNIT DOSE ARTICLES COMPRISING WATER-SOLUBLE FIBROUS STRUCTURES

FIELD OF THE INVENTION

Described herein is a household care composition, which delivers active agents onto fabric, in the form of a fibrous water-soluble unit dose article comprising a water-soluble fibrous structure and one or more particles, as well as methods for making the same.

BACKGROUND OF THE INVENTION

Fibrous water-soluble unit dose articles are desired by consumers as they provide a convenient, efficient, and clean way of dosing a fabric or hard surface treatment composition. Fibrous water-soluble unit dose articles provide a measured dosage of a treatment composition, thereby avoiding over or under dosing. Additionally, fibrous water-soluble unit dose articles create potentially safe handling methods to dose compositions that would not be desirable to handle individually.

Fibrous water-soluble unit dose articles are of increasing interest to consumers. The technology related to such articles continues to advance in terms of providing new compositions having desired active agents with the articles enabling the consumers to do the job that they wish to accomplish. One such desired active is a concentrated acid dose. High concentration acid doses allow for malodor reduction in textiles and fibers. However, low pH acids are not traditionally handled by average consumers. Additionally, the average consumer does not know how to dose acids.

As such there is a need within fibrous water-soluble unit dose articles to formulate fibrous water-soluble unit doses that are capable of delivering an effective amount of low pH acids. Surprisingly, it has been found that fibrous water-soluble unit dose articles comprising high levels of acid, as described herein, can be created while exhibiting desirable dissolution profiles versus other compositions and delivering a consumer benefit.

SUMMARY OF THE INVENTION

Described herein is a fibrous water-soluble unit dose comprising a water-soluble fibrous structure comprising a high concentration of low pH acid.

Further described herein is a fibrous water-soluble unit dose comprising a soluble fibrous structure encasing an active agent, wherein said active agent comprises from 5% to 90% of an active agent acid.

Further described herein is a method for reducing the pH of a wash liquor, the method comprising providing a liquid, providing a fibrous water-soluble article, dissolving the fibrous water-soluble article in the liquid, wherein the liquid pH is reduced to below 6 when combined with the fibrous water-soluble article.

DETAILED DESCRIPTION OF THE INVENTION

Definitions

Figure 1:
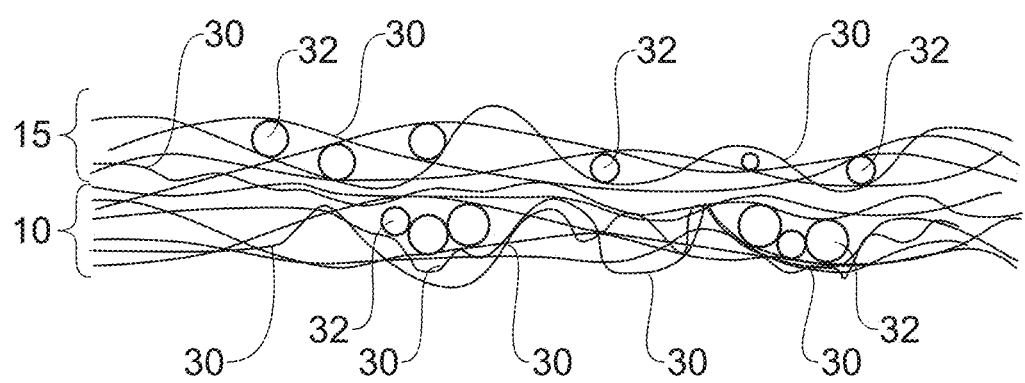
FIG. 1 is a schematic representation of a cross-sectional view of an example of a multiply fibrous structure.

Features and benefits of the present invention will become apparent from the following description, which includes examples intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein, the articles including "the," "a" and "an" when used in a claim or in the specification, are understood to mean one or more of what is claimed or described.

As used herein, the terms "include," "includes" and "including" are meant to be non-limiting.

The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.5%, 0.25%, 0.1%, 0.05%, or 0.01%, or even 0%, by weight of the composition, of the component.

All cited patents and other documents are, in relevant part, incorporated by reference as if fully restated herein. The citation of any patent or other document is not an admission that the cited patent or other document is prior art with respect to the present invention.

In this description, all concentrations and ratios are on a weight basis of the composition unless otherwise specified.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The term "renewable" is synonymous with the terms "biobased," "sustainable," "sustainably derived," or "from sustainable sources" and means bio-derived (derived from a renewable resource, e.g., plants) or "non-geologically derived." "Geologically derived" means derived from, for example, petrochemicals, natural gas, or coal. "Geologically derived" materials cannot be easily replenished or regrown (e.g., in contrast to plant- or algae-produced oils).

As used herein, the term "renewable component" refers to a component that is derived from renewable feedstock and contains renewable carbon. A renewable feedstock is a feedstock that is derived from a renewable resource, e.g., plants, and non-geologically derived. A material may be partially renewable (less than 100% renewable carbon content, from about 1% to about 50% renewable carbon content)

or 100% renewable (100% renewable carbon content). A renewable material may be blended with a nonrenewable material.

"Renewable carbon" may be assessed according to the "Assessment of the Biobased Content of Materials" method, ASTM D6866.

As used herein, the phrases "fibrous water-soluble unit dose article," "water-soluble fibrous unit dose article", "water-soluble fibrous unit dose", "water-soluble fibrous structure", and "water-soluble fibrous element" mean that the unit dose article, fibrous structure, and fibrous element are miscible in water. In other words, the unit dose article, fibrous structure, or fibrous element is capable of forming a homogeneous solution with water at ambient conditions. "Ambient conditions" as used herein means 23° C.±1.0° C. and a relative humidity of 50%±2%. The fibrous water-soluble unit dose article may contain insoluble materials, which are dispersible in aqueous wash conditions to a suspension mean particle size that is less than about 20 microns, or less than about 50 microns.

The fibrous water-soluble unit dose article may include any of the disclosures found in U.S. patent application Ser. No. 15/880,594 filed on Jan. 26, 2018; U.S. patent application Ser. No. 15/880,599 filed Jan. 26, 2018; and U.S. patent application Ser. No. 15/880,604 filed Jan. 26, 2018; incorporated by reference in their entirety.

The fibrous water-soluble unit dose article may comprise of 50% or greater of bio-based materials, such as for example between 50% and 95% bio-based. Some of the individual components of the fibrous water-soluble unit dose article may be fully bio-based to create an article that has a total bio-based content of greater than 50%.

These fibrous water-soluble unit dose articles can be dissolved under various wash conditions, e.g., low temperature, low water and/or short wash cycles or cycles where consumers have been overloading the machine, especially with items having high water absorption capacities, while providing sufficient delivery of active agents for the intended effect on the target consumer substrates (with similar performance as today's liquid products). Furthermore, the fibrous water-soluble unit dose articles described herein can be produced in an economical manner by spinning fibers comprising active agents. The fibrous water-soluble unit dose articles described herein also have improved cleaning performance.

The surface of the fibrous water-soluble unit dose article may comprise a printed area. The printed area may cover between about 10% and about 100% of the surface of the article. The area of print may comprise inks, pigments, dyes, bluing agents or mixtures thereof. The area of print may be opaque, translucent or transparent. The area of print may comprise a single color or multiple colors. The printed area maybe on more than one side of the article and contain instructional text and/or graphics. The surface of the fibrous water-soluble unit dose article may comprise an aversive agent, for example a bittering agent. Suitable bittering agents include, but are not limited to, naringin, sucrose octacetate, quinine hydrochloride, denatonium benzoate, or mixtures thereof. Any suitable level of aversive agent may be used. Suitable levels include, but are not limited to, 1 to 5000 ppm, or even 100 to 2500 ppm, or even 250 to 2000 ppm.

The fibrous water-soluble unit dose may utilize the acid as the bittering agent, preferably citric acid and salts thereof. The citric acid may be combined with any one of the bittering agents previously stated. The citric acid may be used as the bittering agent within the article while a different bittering agent is used on the surface of the article.

The fibrous water-soluble unit dose articles may exhibit a thickness of greater than 0.01 mm and/or greater than 0.05 mm and/or greater than 0.1 mm and/or to about 100 mm and/or to about 50 mm and/or to about 20 mm and/or to about 10 mm and/or to about 5 mm and/or to about 2 mm and/or to about 0.5 mm and/or to about 0.3 mm as measured by the Thickness Test Method described herein.

The fibrous water-soluble unit dose articles may have basis weights of from about 500 grams/m$^2$ to about 5,000 grams/m$^2$, or from about 1,000 grams/m$^2$ to about 4,000 grams/m$^2$, or from about 1,500 grams/m$^2$ to about 3,500 grams/m$^2$, or from about 2,000 grams/m$^2$ to about 3,000 grams/m$^2$, as measured according to the Basis Weight Test Method described herein.

The fibrous water-soluble unit dose article may exhibit different regions, such as different regions of basis weight, density, caliper, and/or wetting characteristics. The fibrous water-soluble unit dose article may be compressed at the point of edge sealing. The fibrous water-soluble unit dose article may comprise texture on one or more of its surfaces. A surface of the fibrous water-soluble unit dose article may comprise a pattern, such as a non-random, repeating pattern. The fibrous water-soluble unit dose article may comprise apertures. The fibrous water-soluble unit dose article may comprise a fibrous structure having discrete regions of fibrous elements that differ from other regions of fibrous elements in the structure. The fibrous water-soluble unit dose article may be used as is or it may be coated with one or more active agents.

The fibrous water-soluble unit dose article may comprise one or more plies. The fibrous water-soluble unit dose article may comprise at least two and/or at least three and/or at least four and/or at least five plies. The fibrous plies can be fibrous structures. Each ply may comprise one or more layers, for example one or more fibrous element layers, one or more particle layers, and/or one or more fibrous element/particle mixture layers. The layer(s) may be sealed. In particular, particle layers and fibrous element/particle mixture layers may be sealed, such that the particles do not leak out. The fibrous water-soluble unit dose articles may comprise multiple plies, where each ply comprises two layers, where one layer is a fibrous element layer and one layer is a fibrous element/particle mixture layer, and where the multiple plies are sealed (e.g., at the edges) together. Sealing may inhibit the leakage of particles as well as help the unit dose article maintain its original structure. However, upon addition of the fibrous water-soluble unit dose article to water, the unit dose article dissolves and releases the particles into the wash liquor.

The fibrous water-soluble unit dose may be in the form of any three-dimensional structure. The fibrous water-soluble unit dose article can be perforated. The article can also be cut or shaped into various sizes for different intended uses. For example, the fibrous water-soluble unit dose may be in the form of a square, a rounded square, a kite, a rectangle, a triangle, a circle, an ellipse, and mixtures thereof.

The fibrous water-soluble unit dose may comprise less than 10 ingredients. The fibrous water-soluble unit dose may comprise between 3 and 9 ingredients, such as, for example, 4 ingredients, 5 ingredients, 6 ingredients, 7 ingredients, or 8 ingredients.

The fibrous water-soluble unit dose articles disclosed herein comprise a water-soluble fibrous structure and one or more particles. The water-soluble fibrous structure may comprise a plurality of fibrous elements, for example a plurality of filaments. The one or more particles, for example one or more active agent-containing particles, may be distributed throughout the structure. The fibrous water-soluble unit dose article may comprise a plurality of two or more and/or three or more fibrous elements that are inter-entangled or otherwise associated with one another to form a fibrous structure and one or more particles, which may be distributed throughout the fibrous structure.

The fibrous water-soluble unit dose article may comprise a water-soluble fibrous structure and a plurality of particles distributed throughout the structure, where the water-soluble fibrous structure comprises a plurality of identical or substantially identical, from a compositional perspective, fibrous elements. The water-soluble fibrous structure may comprise two or more different fibrous elements. Non-limiting examples of differences in the fibrous elements may be physical differences, such as differences in diameter, length, texture, shape, rigidness, elasticity, and the like; chemical differences, such as crosslinking level, solubility, melting point, Tg, active agent, filament-forming material, color, level of active agent, basis weight, level of filament-forming material, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use. Two or more fibrous elements within the fibrous structure may comprise different active agents. This may be the case where the different active agents may be incompatible with one another, for example an anionic surfactant and a cationic polymer. When using different fibrous elements, the resulting structure may exhibit different wetting, imbibitions, and solubility characteristics.

Fibrous Structure

Fibrous structures comprise one or more fibrous elements. The fibrous elements can be associated with one another to form a structure. Fibrous structures can include particles within and or on the structure. Fibrous structures can be homogeneous, layered, unitary, zoned, or as otherwise desired, with different active agents defining the various aforesaid portions.

A fibrous structure can comprise one or more layers, the layers together forming a ply.

Fibrous Elements

The fibrous elements may be water-soluble. The fibrous elements may comprise one or more filament-forming materials and/or one or more active agents, such as a surfactant. The one or more active agents may be releasable from the fibrous element, such as when the fibrous element and/or fibrous structure comprising the fibrous element is exposed to conditions of intended use.

The fibrous elements may be spun from a filament-forming composition, also referred to as fibrous element-forming compositions, via suitable spinning process operations, such as meltblowing, spunbonding, electro-spinning, and/or rotary spinning.

"Filament-forming composition" and/or "fibrous element-forming composition" as used herein means a composition that is suitable for making a fibrous element such as by meltblowing and/or spunbonding. The filament-forming composition comprises one or more filament-forming materials that exhibit properties that make them suitable for spinning into a fibrous element. The filament-forming material may comprise a polymer. In addition to one or more filament-forming materials, the filament-forming composition may comprise one or more active agents, for example, a surfactant. In addition, the filament-forming composition may comprise one or more polar solvents, such as water, into which one or more, for example all, of the filament-forming materials and/or one or more, for example all, of the active agents are dissolved and/or dispersed prior to spinning a fibrous element, such as a filament from the filament-forming composition.

The filament-forming composition may comprise two or more different filament-forming materials. Thus, the fibrous elements may be monocomponent (one type of filament-forming material) and/or multicomponent, such as bicomponent. The two or more different filament-forming materials may be randomly combined to form a fibrous element. The two or more different filament-forming materials may be orderly combined to form a fibrous element, such as a core and sheath bicomponent fibrous element, which is not considered a random mixture of different filament-forming materials for purposes of the present disclosure. Bicomponent fibrous elements may be in any form, such as side-by-side, core and sheath, islands-in-the-sea and the like.

The fibrous elements may be substantially free of alkylalkoxylated sulfate. Each fibrous element may comprise from about 0%, or from about 0.1%, or from about 5%, or from about 10%, or from about 15%, or from about 20%, or from about 25%, or from about 30%, or from about 35%, or from about 40% to about 0.2 or to about 1%, or to about 5%, or to about 10%, or to about 15%, or to about 20%, or to about 25%, or to about 30%, or to about 35% or to about 40%, or to about 50% by weight on a dry fibrous element basis of an alkylalkoxylated sulfate. The amount of alkylalkoxylated sulfate in each of the fibrous elements is sufficiently small so as not to affect the processing stability and film dissolution thereof. Alkylalkoxylated sulfates, when dissolved in water, may undergo a highly viscous hexagonal phase at certain concentration ranges, e.g., 30-60% by weight, resulting in a gel-like substance. Therefore, if incorporated into the fibrous elements in a significant amount, alkylalkoxylated sulfates may significantly slow down the dissolution of the fibrous water-soluble unit dose articles in water, and worse yet, result in undissolved solids afterwards. Correspondingly, most of such surfactants are formulated into the particles.

The fibrous elements may each contain at least one filament-forming material and an active agent, preferably a surfactant. The surfactant may have a relatively low hydrophilicity, as such a surfactant is less likely to form a viscous, gel-like hexagonal phase when being diluted. By using such a surfactant in forming the filaments, gel-formation during wash may be effectively reduced, which in turn may result in faster dissolution and low or no residues in the wash. The surfactant can be selected, for example, from the group consisting of unalkoxylated $C_6$-$C_{20}$ linear or branched alkyl sulfates (AS), $C_6$-$C_{20}$ linear alkylbenzene sulfonates (LAS), and combinations thereof. The surfactant may be a $C_6$-$C_{20}$ linear alkylbenzene sulfonates (LAS). LAS surfactants are well known in the art and can be readily obtained by sulfonating commercially available linear alkylbenzenes. Exemplary $C_6$-$C_{20}$ linear alkylbenzene sulfonates that can be used include alkali metal, alkaline earth metal or ammonium salts of $C_6$-$C_{20}$ linear alkylbenzene sulfonic acids, such as the sodium, potassium, magnesium and/or ammonium salts of $C_{11}$-$C_{18}$ or $C_{11}$-$C_{14}$ linear alkylbenzene sulfonic acids. The sodium or potassium salts of $C_{12}$ linear alkylbenzene sulfonic acids, for example, the sodium salt of $C_{12}$ linear alkylbenzene sulfonic acid, i.e., sodium dodecylbenzene sulfonate, may be used as the first surfactant.

The fibrous element may comprise at least about 5%, and/or at least about 10%, and/or at least about 15%, and/or at least about 20%, and/or less than about 80%, and/or less than about 75%, and/or less than about 65%, and/or less than about 60%, and/or less than about 55%, and/or less than about 50%, and/or less than about 45%, and/or less than about 40%, and/or less than about 35%, and/or less than about 30%, and/or less than about 25% by weight on a dry fibrous element basis and/or dry fibrous structure basis of the filament-forming material and greater than about 20%, and/or at least about 35%, and/or at least about 40%, and/or at least about 45%, and/or at least about 50%, and/or at least about 55%, and/or at least about 60%, and/or at least about 65%, and/or at least about 70%, and/or less than about 95%, and/or less than about 90%, and/or less than about 85%, and/or less than about 80%, and/or less than about 75% by weight on a dry fibrous element basis and/or dry fibrous structure basis of an active agent, preferably surfactant. The fibrous element may comprise greater than about 80% by weight on a dry fibrous element basis and/or dry fibrous structure basis of surfactant.

Preferably, each fibrous element may be characterized by a sufficiently high total surfactant content, e.g., at least about 30%, or at least about 40%, or at least about 50%, or at least about 60%, or at least about 70%, by weight on a dry fibrous element basis and/or dry fibrous structure basis of the first surfactant.

The total level of filament-forming materials present in the fibrous element may be from about 5% to less than about 80% by weight on a dry fibrous element basis and/or dry fibrous structure basis and the total level of surfactant present in the fibrous element may be greater than about 20% to about 95% by weight on a dry fibrous element basis and/or dry fibrous structure basis.

One or more of the fibrous elements may comprise at least one additional surfactant selected from the group consisting of other anionic surfactants (i.e., other than AS and LAS), nonionic surfactants, zwitterionic surfactants, amphoteric surfactants, cationic surfactants, and combinations thereof.

Other suitable anionic surfactants include $C_6$-$C_{20}$ linear or branched alkyl sulfonates, $C_6$-$C_{20}$ linear or branched alkyl carboxylates, $C_6$-$C_{20}$ linear or branched alkyl phosphates, $C_6$-$C_{20}$ linear or branched alkyl phosphonates, $C_6$-$C_{20}$ alkyl N-methyl glucose amides, $C_6$-$C_{20}$ methyl ester sulfonates (MES), and combinations thereof.

Suitable nonionic surfactants include alkoxylated fatty alcohols. The nonionic surfactant may be selected from ethoxylated alcohols and ethoxylated alkyl phenols of the formula $R(OC_2H_4)_nOH$, wherein R is selected from the group consisting of aliphatic hydrocarbon radicals containing from about 8 to about 15 carbon atoms and alkyl phenyl radicals in which the alkyl groups contain from about 8 to about 12 carbon atoms, and the average value of n is from about 5 to about 15. Non-limiting examples of nonionic surfactants useful herein include: $C_8$-$C_{18}$ alkylethoxylates, such as, NEODOL® nonionic surfactants from Shell; $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, BA; $C_{14}$-$C_{22}$ mid-chain branched alkylalkoxylates, $BAE_x$, wherein x is from 1 to 30; alkylpolysaccharides; specifically alkylpolyglycosides; polyhydroxy fatty acid amides; and ether capped poly(oxyalkylated) alcohol surfactants. Suitable nonionic detersive surfactants also include alkyl polyglucoside and alkylalkoxylated alcohol. Suitable nonionic surfactants also include those sold under the tradename Lutensol® from BASF.

Non-limiting examples of cationic surfactants include: the quaternary ammonium surfactants, which can have up to 26 carbon atoms include: alkoxylate quaternary ammonium (AQA) surfactants; dimethyl hydroxyethyl quaternary ammonium; dimethyl hydroxyethyl lauryl ammonium chloride; polyamine cationic surfactants; cationic ester surfactants; and amino surfactants, e.g., amido propyldimethyl amine (APA). Suitable cationic detersive surfactants also include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

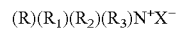

$$(R)(R_1)(R_2)(R_3)N^+X^-$$

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, for example chloride; sulfate; and sulfonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Suitable examples of zwitterionic surfactants include: derivatives of secondary and tertiary amines, including derivatives of heterocyclic secondary and tertiary amines; derivatives of quaternary ammonium, quaternary phosphonium or tertiary sulfonium compounds; betaines, including alkyl dimethyl betaine, cocodimethyl amidopropyl betaine, and sulfo and hydroxy betaines; $C_8$ to $C_{18}$ (e.g., from $C_{12}$ to $C_{18}$) amine oxides; N-alkyl-N,N-dimethylammino-1-propane sulfonate, where the alkyl group can be $C_8$ to $C_{18}$.

Suitable amphoteric surfactants include aliphatic derivatives of secondary or tertiary amines, or aliphatic derivatives of heterocyclic secondary and tertiary amines in which the aliphatic radical may be straight or branched-chain and where one of the aliphatic substituents contains at least about 8 carbon atoms, or from about 8 to about 18 carbon atoms, and at least one of the aliphatic substituents contains an anionic water-solubilizing group, e.g. carboxy, sulfonate, sulfate. Suitable amphoteric surfactants also include sarcosinates, glycinates, taurinates, and mixtures thereof.

The fibrous elements may comprise a surfactant system containing only anionic surfactants, e.g., either a single anionic surfactant or a combination of two or more different anionic surfactants. Alternatively, the fibrous elements may include a composite surfactant system, e.g., containing a combination of one or more anionic surfactants with one or more nonionic surfactants, or a combination of one or more anionic surfactants with one or more zwitterionic surfactants, or a combination of one or more anionic surfactants with one or more amphoteric surfactants, or a combination of one or more anionic surfactants with one or more cationic surfactants, or a combination of all the above-mentioned types of surfactants (i.e., anionic, nonionic, amphoteric and cationic).

In general, fibrous elements are elongated particulates having a length greatly exceeding average diameter, e.g., a length to average diameter ratio of at least about 10. A fibrous element may be a filament or a fiber. Filaments are relatively longer than fibers. A filament may have a length of greater than or equal to about 5.08 cm (2 in.), and/or greater than or equal to about 7.62 cm (3 in.), and/or greater than or equal to about 10.16 cm (4 in.), and/or greater than or equal to about 15.24 cm (6 in.). A fiber may have a length of less than about 5.08 cm (2 in.), and/or less than about 3.81 cm (1.5 in.), and/or less than about 2.54 cm (1 in.).

The one or more filament-forming materials and active agents may be present in the fibrous element at a weight ratio of total level of filament-forming materials to active agents of about 2.0 or less, and/or about 1.85 or less, and/or less than about 1.7, and/or less than about 1.6, and/or less than about 1.5, and/or less than about 1.3, and/or less than about 1.2, and/or less than about 1, and/or less than about 0.7, and/or less than about 0.5, and/or less than about 0.4, and/or less than about 0.3, and/or greater than about 0.1, and/or greater than about 0.15, and/or greater than about 0.2. The one or more filament-forming materials and active agents may be present in the fibrous element at a weight ratio of total level of filament-forming materials to active agents of about 0.2 to about 0.7.

The fibrous element may comprise from about 10% to less than about 80% by weight on a dry fibrous element basis and/or dry fibrous structure basis of a filament-forming material, such as polyvinyl alcohol polymer, starch polymer, and/or carboxymethylcellulose polymer, and greater than about 20% to about 90% by weight on a dry fibrous element basis and/or dry fibrous structure basis of an active agent, such as surfactant. The fibrous element may further comprise a plasticizer, such as glycerin, and/or additional pH adjusting agents, such as citric acid. The fibrous element may have a weight ratio of filament-forming material to active agent of about 2.0 or less. The filament-forming material may be selected from the group consisting of polyvinyl alcohol, starch, carboxymethylcellulose, polyethylene oxide, and other suitable polymers, especially hydroxyl-containing polymers and their derivatives. The filament-forming material may range in weight average molecular weight from about 100,000 g/mol to about 3,000,000 g/mol. It is believed that in this range, the filament-forming material may provide extensional rheology, without being so elastic that fiber attenuation is inhibited in the fiber-making process.

The one or more active agents may be releasable and/or released when the fibrous element and/or fibrous structure comprising the fibrous element is exposed to conditions of intended use. The one or more active agents in the fibrous element may be selected from the group consisting of surfactants, organic polymeric compounds, and mixtures thereof.

The fibrous elements may exhibit a diameter of less than about 300 µm, and/or less than about 75 µm, and/or less than about 50 µm, and/or less than about 25 µm, and/or less than about 10 µm, and/or less than about 5 µm, and/or less than about 1 µm as measured according to the Diameter Test Method described herein. The fibrous elements may exhibit a diameter of greater than about 1 µm as measured according to the Diameter Test Method described herein. The diameter of a fibrous element may be used to control the rate of release of one or more active agents present in the fibrous element and/or the rate of loss and/or altering of the fibrous element's physical structure.

The fibrous element may comprise two or more different active agents, which are compatible or incompatible with one another. The fibrous element may comprise an active agent within the fibrous element and an active agent on an external surface of the fibrous element, such as an active agent coating on the fibrous element. The active agent on the external surface of the fibrous element may be the same or different from the active agent present in the fibrous element. If different, the active agents may be compatible or incompatible with one another. The one or more active agents may be uniformly distributed or substantially uniformly distributed throughout the fibrous element. The one or more active agents may be distributed as discrete regions within the fibrous element.

Active Agents

The fibrous water-soluble unit dose articles described herein may contain one or more active agents. The active agents may be present in the fibrous elements in the form of distinct particles, in the form of or integrated into particles, or as a premix in the article. Premixes for example, may be slurries of active agents that are combined with aqueous absorbents.

The active agent may be an acid in the form of an active agent acid or an acid. Examples of acids suitable for use include, but are not limited to, organic acids selected from the group consisting of acetic acid, adipic acid, aspartic acid, carboxymethyloxymalonic acid, carboxymethyloxysuccinic acid, citric acid, benzoic acid, formic acid, glutaric acid, glutonic acid, hydroxyethyliminodiacetic acid, iminodiacetic acid, lactic acid, maleic acid, malic acid, malonic acid, oxydiacetic acid, oxydisuccinic acid, succinic acid, sulfamic acid, tartaric acid, tartaric-disuccinic acid, tartaric-monosuccinic acid, their salts or mixtures thereof, either alone or in combination. Preferably, the acid is citric acid, lactic acid, acetic acid, and/or tartaric acid, and more preferably citric acid.

In certain aspects, the acid comprises a coating. The coating can help prevent the active agent from prematurely dissolving. A preferred acid is citric acid and preferred coatings include maltodextrin, waxes, citrate, sulfate, zeolites, anti-caking agents such as silicon dioxide or other desiccants. Preferred combinations include citric acid coated with maltodextrin (available under the tradename Citric Acid DC), citric acid coated with citrate (available under the tradename CITROCOAT® N), or citric acid coated with silicon dioxide (available under the tradename Citric Acid S40).

The active agent acid may be incorporated into the fibrous water-soluble unit dose composition at a level of from about 5% to about 90%, preferably from about 10% to about 80%, preferably from about 15% to about 75%, preferably from about 40% to about 70%, preferably from about 60% to about 70%, by weight of the fibrous water-soluble unit dose article, such as, for example, 20%, 25%, 30%, 35%, 40%, 45%, 50%, 55%, 60%, 65%, 70%, 75%, or 80% by weight of the fibrous water-soluble unit dose article. The active agent acid may be incorporated as distinct particles, a encapsulated particles, as particles in a slurry, as part of the fibers, or as a mixture thereof.

The fibrous water-soluble unit dose may comprise one or more additional organic acids. The additional organic acid may be in the form of an organic carboxylic acid or polycarboxylic acid. Examples of organic acids that may be used include: acetic acid, adipic acid, aspartic acid, benzoic acid, carboxymethyloxymalonic acid, carboxymethyloxysuccinic acid, citric acid, formic acid, glycolic acid, benzoic acid, gluconic acid, glutaric acid, hydroxyethyliminodiacetic acid, iminodiacetic acid, lactic acid, maleic acid, malic acid, malonic acid, oxydiacetic acid, oxydisuccinic acid, succinic acid, sulfamic acid, tartaric acid, tartaricdisuccinic acid, tartaric-monosuccinic acid, their salts or mixtures thereof. In some aspects, the composition comprises organic acids that can also serve as detergent builders, such as citric acid.

The water soluble unit dose may further comprise acids with a pKa of from about 1.0 to about 5.0. Suitable acids within this pKa range can be found but not limited to those in the CRC Handbook of Chemistry and Physics, 99$^{th}$ edition, Taylor & Francis.

The organic acid may be a water-soluble or water-miscible acid. In some aspects, the organic acid has a solubility in water at 20° C. of at least about 10 g acid/100 ml water, or at least about 30 g acid/100 ml water, or at least about 50 g acid/100 ml water, or at least about 70 g acid/100 ml water, or at least about 85 g/100 ml water. In some aspects, the composition is substantially free of fatty acid.

The organic acid may be a low-weight acid, for example, an acid having a molecular weight of less than 210 g/mole. In some aspects, the organic acid has no more than nine carbon atoms, alternatively no more than six carbon atoms. The organic acid in the detergent composition may have no more than four carbon atoms, or no more than three carbon atoms, or fewer than three carbon atoms. Specific examples of organic acids having fewer than three carbon atoms include formic acid and acetic acid.

FIG. 1 shows a first ply 10 and a second ply 15 associated with the first ply 10, wherein the first ply 10 and the second ply 15 each comprises a plurality of fibrous elements 30, in this case filaments, and a plurality of particles 32 (active agent acid here in the form of citric acid). In the second ply 15, the particles 32 are dispersed randomly, in the x, y, and z axes, and in the first ply, the particles 32 are in pockets.

Figure 2:
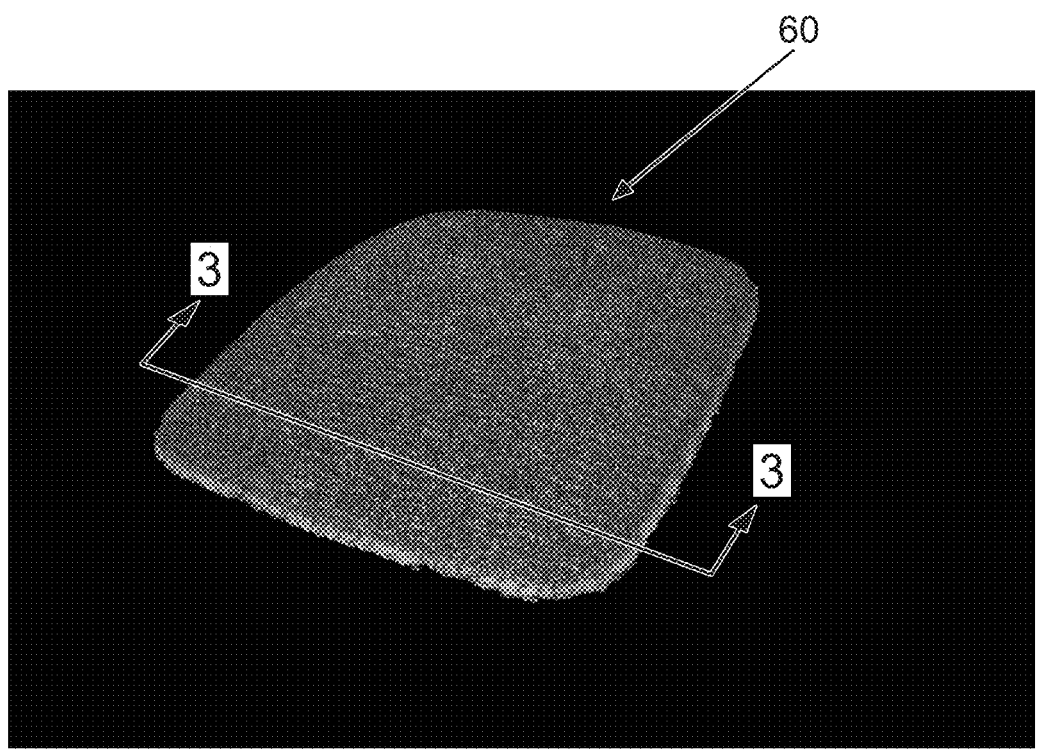
FIG. 2 is a perspective view of an example of a fibrous water-soluble unit dose article.

FIG. 2 is a perspective view of a fibrous water-soluble unit dose 60.

Figure 3:
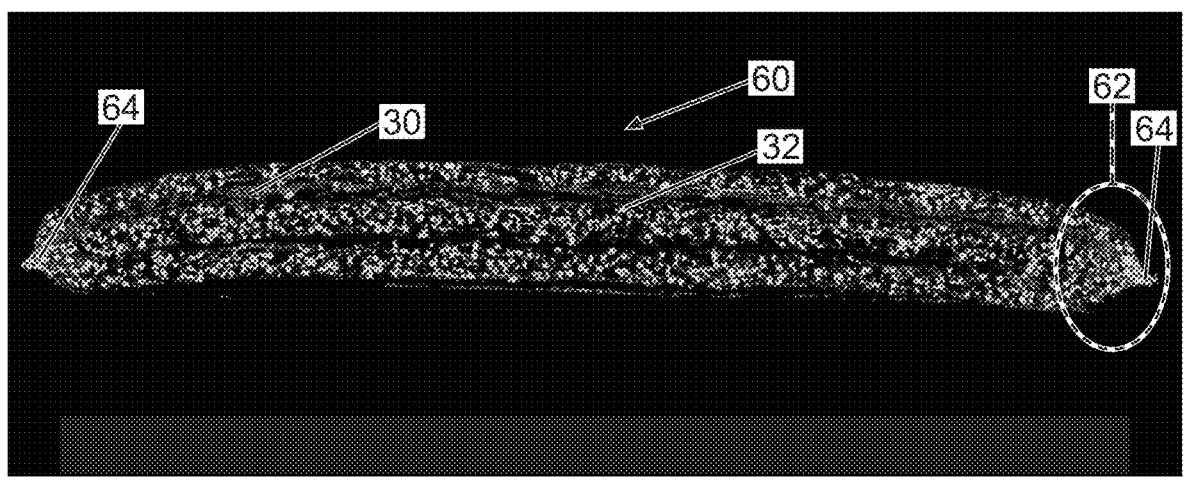
FIG. 3 is a micro-CT scan image showing a cross-sectional view of the example of a fibrous water-soluble unit dose article taken along line 3-3.

FIG. 3 is a micro-CT scan image showing a cross-sectional view of an example of the fibrous water-soluble unit dose article of FIG. 2 taken along line 3-3. The fibrous water-soluble unit dose having a fibrous element layer and a fibrous element/particle mixture layer. The fibrous water-soluble unit dose comprises a plurality of fibrous elements 30, in this case filaments, and a plurality of particles 32. The multiply, multilayer article is sealed at the edges 64, so that the particles do not leak out. The outer surfaces of the article are fibrous element layers. As shown in FIG. 3, the particles 32 do not agglomerate between the fibers and can be seen as individual particles.

Figure 4:
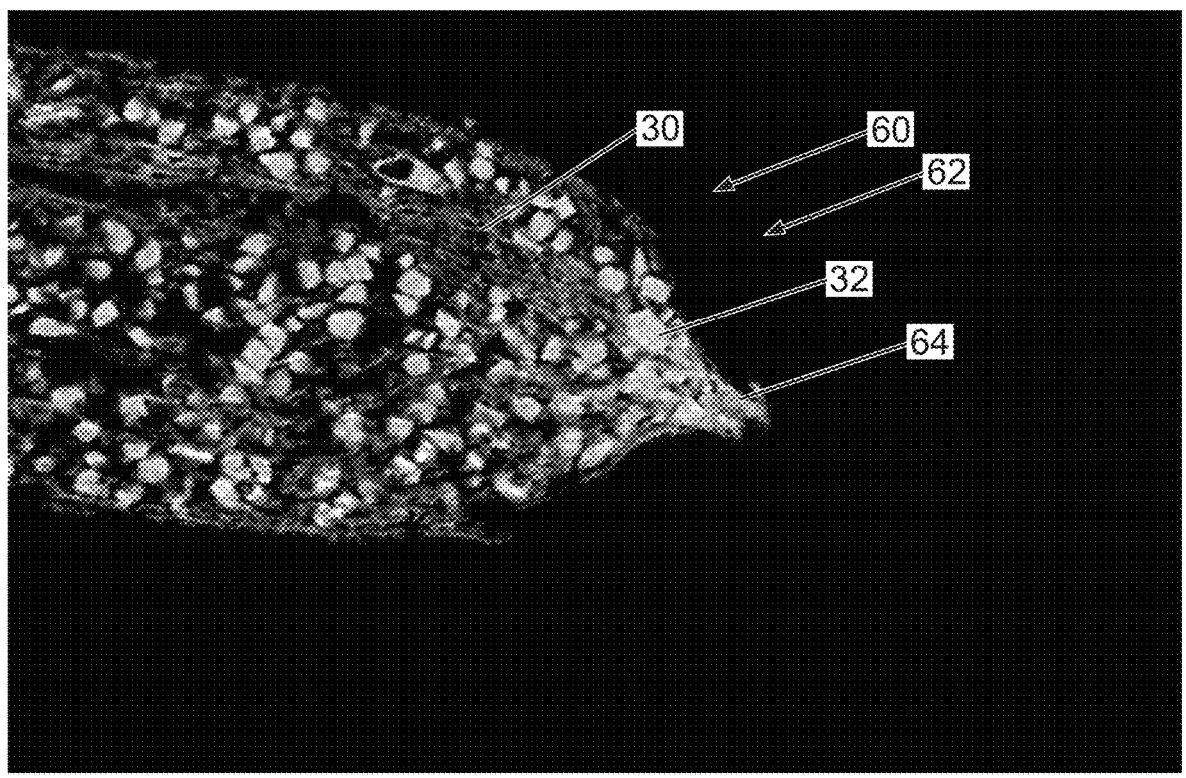
FIG. 4 is a magnified view of a portion of FIG. 3.

FIG. 4 is a magnified view 62 of a portion of FIG. 3. As shown in FIG. 4, the sealing edge 64 of the fibrous water-soluble unit dose 60 comprises of one or more particles 32 of citric acid.

The fibrous elements and/or particles may be arranged within the fibrous water-soluble unit dose article, in a single ply or in multiple plies, to provide the article with two or more regions that comprise different active agents. For example, one region of the article may comprise bleaching agents and/or surfactants and another region of the article may comprise softening agents.

The fibrous water-soluble unit dose article can be viewed hierarchically starting from the form in which the consumer interacts with the water-soluble article and working backward to the raw materials from which the water-soluble article is made, e.g., plies, fibrous structures, and particles. The fibrous plies can be fibrous structures.

The fibrous water-soluble unit dose may comprise additional components selected from the group consisting of a surfactant, a structurant, a builder, an organic polymeric compound, an enzyme, an enzyme stabilizer, a bleach system, a brightener, a hueing agent, a chelating agent, a suds suppressor, a conditioning agent, a humectant, a perfume, a perfume microcapsule, a filler or carrier, an alkalinity system, a pH control system, a buffer, an alkanolamine, and mixtures thereof.

Solid carrier: The fibrous water-soluble unit dose may comprise a suitable solid carriers include inorganic salts, such as sodium carbonate, sodium sulfate and mixtures thereof. Other preferred solid carriers include aluminosilicates, such as zeolite, dried dispersant polymer in a fine powder form, and absorbent grades of fumed or precipitated silica (for example, precipitated hydrophilic silica commercialized by Evonik Industries AG under the trade name SN340). Mixtures of solid carrier materials may also be used.

Surfactant

The fibrous water-soluble unit dose may comprise a surfactant in addition to a surfactant in the fibers. The surfactant may be selected from the group consisting of anionic surfactants, nonionic surfactants, cationic surfactants, zwitterionic surfactants, amphoteric surfactants, ampholytic surfactants, and mixtures thereof. These surfactants are described in more detail above.

Encapsulates

The fibrous water-soluble unit dose may comprise an encapsulate. The encapsulate may comprise a core, a shell having an inner and outer surface, said shell encapsulating said core. The core may comprise any laundry care adjunct, though typically the core may comprise material selected from the group consisting of perfumes; brighteners; hueing dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinylalcohols, optionally containing other co-monomers; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

Preferred encapsulates comprise perfume. Preferred encapsulates comprise a shell which may comprise melamine formaldehyde and/or cross linked melamine formaldehyde. Other preferred capsules comprise a polyacrylate based shell. Preferred encapsulates comprise a core material and a shell, said shell at least partially surrounding said core material, is disclosed. At least 75%, 85% or even 90% of said encapsulates may have a fracture strength of from 0.2 MPa to 10 MPa, and a benefit agent leakage of from 0% to 20%, or even less than 10% or 5% based on total initial encapsulated benefit agent. Preferred are those in which at least 75%, 85% or even 90% of said encapsulates may have (i) a particle size of from 1 microns to 80 microns, 5 microns to 60 microns, from 10 microns to 50 microns, or even from 15 microns to 40 microns, and/or (ii) at least 75%, 85% or even 90% of said encapsulates may have a particle wall thickness of from 30 nm to 250 nm, from 80 nm to 180 nm, or even from 100 nm to 160 nm. Formaldehyde scavengers may be employed with the encapsulates, for example, in a capsule slurry and/or added to a composition before, during or after the encapsulates are added to such composition.

Suitable capsules that can be made using known processes. Alternatively, suitable capsules can be purchased from Encapsys LLC of Appleton, Wisconsin USA. In a preferred aspect the composition may comprise a deposition aid, preferably in addition to encapsulates. Preferred deposition aids are selected from the group consisting of cationic and nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or more monomers selected from the group comprising acrylic acid and acrylamide.

Perfumes

The fibrous water-soluble unit dose may comprise a perfume either in the fibers, separate from the fibers, in an encapsulate, or a combination thereof. Non-limiting examples of perfume and perfumery ingredients include, but are not limited to, aldehydes, ketones, esters, and the like. Other examples include various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes may be included at a concentration ranging from about 0.01% to about 2% by weight of the detergent composition.

Dye Transfer Inhibiting Agents

The fibrous water-soluble unit dose may comprise a dye transfer inhibiting agent. Dye transfer inhibiting agents are effective for inhibiting the transfer of dyes from one fabric to another during the cleaning process. Generally, such dye transfer inhibiting agents may include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents may be used at a concentration of about 0.0001% to about 10%, by weight of the composition, in some examples, from about 0.01% to about 5%, by weight of the composition, and in other examples, from about 0.05% to about 2% by weight of the composition.

Suds Suppressors

The fibrous water-soluble unit dose may comprise a suds suppressor or a compounds for reducing or suppressing the formation of suds. Suds suppression can be of particular importance in the so-called "high concentration cleaning process" and in front-loading style washing machines. Examples of suds suppressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols.

Additional suitable antifoams are those derived from phenylpropylmethyl substituted polysiloxanes.

The fibrous water-soluble unit dose may comprise a suds suppressor selected from organomodified silicone polymers with aryl or alkylaryl substituents combined with silicone resin and a primary filler, which is modified silica. The detergent compositions may comprise from about 0.001% to about 4.0%, by weight of the composition, of such a suds suppressor.

The fibrous water-soluble unit dose may comprise a suds suppressor selected from: a) mixtures of from about 80 to about 92% ethylmethyl, methyl(2-phenylpropyl) siloxane; from about 5 to about 14% MQ resin in octyl stearate; and from about 3 to about 7% modified silica; b) mixtures of from about 78 to about 92% ethylmethyl, methyl(2-phenylpropyl) siloxane; from about 3 to about 10% MQ resin in octyl stearate; from about 4 to about 12% modified silica; or c) mixtures thereof, where the percentages are by weight of the anti-foam.

Suds Boosters

If high sudsing is desired, suds boosters such as the $C_{10}$-$C_{16}$ alkanolamides may be used. Some examples include the $C_{10}$-$C_{14}$ monoethanol and diethanol amides. If desired, water-soluble magnesium and/or calcium salts such as $MgCl_2$, $MgSO_4$, $CaCl_2$), $CaSO_4$, and the like, may be added at levels of about 0.1% to about 2% by weight of the detergent composition, to provide additional suds and to enhance grease removal performance.

Conditioning Agents

Suitable conditioning agents include high melting point fatty compounds. The high melting point fatty compound useful herein has a melting point of 25° C. or higher, and is selected from the group consisting of fatty alcohols, fatty acids, fatty alcohol derivatives, fatty acid derivatives, and mixtures thereof. Suitable conditioning agents also include nonionic polymers and conditioning oils, such as hydrocarbon oils, polyolefins, and fatty esters.

Suitable conditioning agents include those conditioning agents characterized generally as silicones (e.g., silicone oils, polyoils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

pH in Wash Liquor

The fibrous water-soluble unit dose articles described herein may be formulated such that, during use in aqueous cleaning operations, the wash water will have a pH of between about 2.0 and about 8, and in some examples, between about 3.0 and about 7, between about 3.5 and about 6, between about 4 to about 5. Techniques for controlling pH at recommended usage levels include the use of buffers, alkalis, or acids, and are well known to those skilled in the art. These include, but are not limited to, the use of sodium carbonate, citric acid or sodium citrate, lactic acid or lactate, monoethanol amine or other amines, boric acid or borates, and other pH-adjusting compounds well known in the art.

Method for Making

Figure 5:
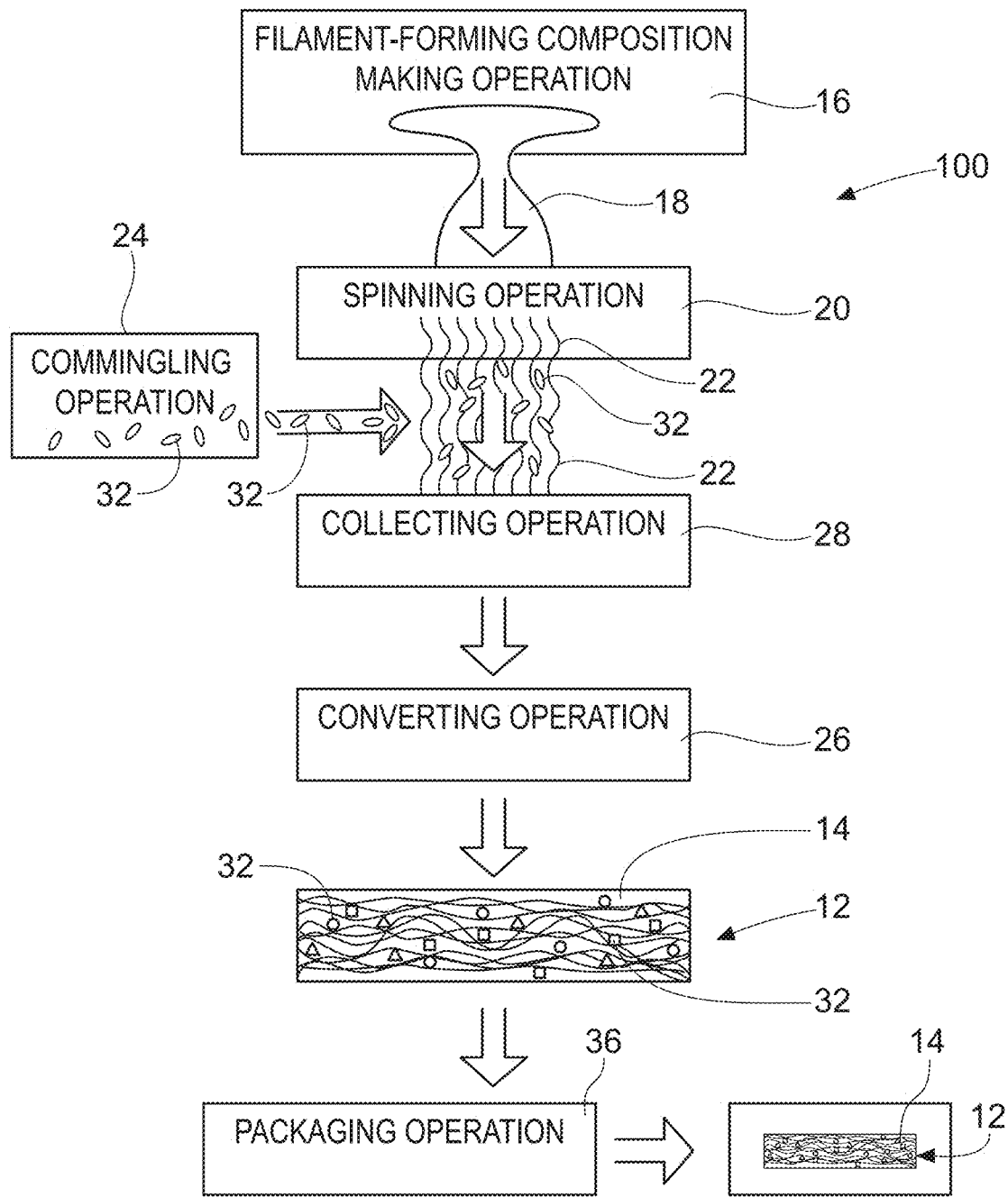
FIG. 5 is a schematic representation of an example of a process for making a fibrous structure.

FIG. 5 illustrates a process 100 of making an article in the form of a co-form. While filaments 22 are being formed, the particle source is turned on and particles 32 are introduced into the filament 22 stream. Filaments may be formed from a Filament-Forming Composition Making Operation 16 that leads to a spinning operation 20. The particles 32 are commingled in a Comingling Operation 24 and then comingled with the filaments 22 within a spinning enclosure. The commingled filaments 22 and particles 32 are collected on a collection device in a collection operation 28 (e.g. a forming belt) as a composite structure (filaments 22 and particles 32 commingled together). The material may then pass through a converting operation 26. The composite structure is referred to as a fibrous structure 14 in the form of a co-form. Finally, a packaging operation 36 may package the fibrous structures into containers 34.

Figure 6:
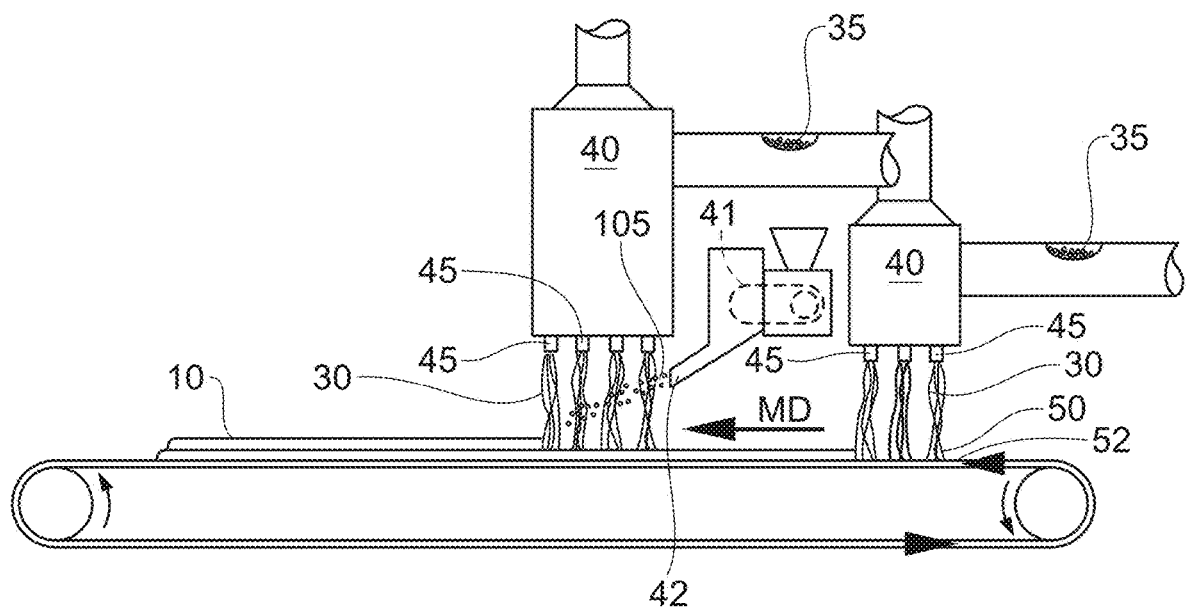
FIG. 6 is a process for making a fibrous structure.

As exemplified by illustration in FIG. 6, a solution of a filament forming composition 35 is provided. The filament forming composition can comprise one or more filament firming materials. The filament forming composition 35 is passed through one or more die block assemblies 40 comprising a plurality of spinnerets 45 to form a plurality of fibrous elements 30 comprising the one or more filament forming materials and optionally one or more optionally active agents such as surfactants. Multiple die block assemblies 40 can be employed to spin different layers of fibrous elements 30, with the fibrous elements 30 of different layers having a composition that differ from one another or are the same as one another. More than two die block assemblies in series can be provided to form three, four, or any other integer number of layers in a given ply. The fibrous elements 30 can be deposited on a belt 50 moving in a machine direction MD to form a first ply 10.

Particles in the form of citricoat can be introduced into the stream of the fibrous elements 30 between the die block assembly 40 and the belt 50. Particles can be fed from a particle receiver onto a belt feeder 41 or optionally a screw feeder. The belt feeder 41 can be set and controlled to deliver the desired mass of particles into the process. The belt feeder can feed an air knife 42 that suspends and directs the particles in an air stream into the fibrous elements 30 to form a particle-fiber layer of comingled fibrous elements 30 and particles that is subsequently deposited on the belt 50.

To form the fibrous water-soluble unit dose, a first ply 10 can be provided. A second ply 15 can be provided separate from the first ply 10. The first ply 10 and the second ply 15 are superposed with one another. By superposed it is meant that one is positioned above or below the other with the proviso that additional plies or other materials, for example active agents, may be positioned between the superposed plies. A portion of the first ply 10 can be joined to a portion of the second ply 15 to form the fibrous water-soluble unit dose 5. Each ply may comprise one or more layers.

The layers may be sealed at the end using any type of seal known including and not limited to ultrasound, pressure, heat, the use of water-soluble adhesives, and combinations thereof. The seal is preferably made using a pressure seal. Without being bound by theory, it is believed that the webs containing acids which have less than 40% relative humidity are difficult to seal via a pressure or heat seal because the individual particles impede the sealing process. Once the relative humidity is greater than 40%, the particles are more malleable and allow for the fibers to be sealed using pressure and or heat.

During the method of making the fibrous water-soluble unit dose comprising a high level of acid, it has been found that one must have the appropriate conditions for the making process. Specifically, it has been surprisingly found that relative humidity must be controlled within a narrow range of 40% to 75% relative humidity for a fibrous water-soluble unit dose comprising a high level of acid as exemplified by Example 1 below. Without being bound by theory, it is believed that the citric acid must be processed at a relative humidity greater than 40% to below 75% to maintain a desirable level of processability while not absorbing a significant amount of atmospheric moisture, such as, for example, 45%, 50%, 55%, 60%, 65%, and 70%. It has surprisingly been found that, processing at a relative humidity below about 40%, one is not able to form a seal with two-plys comprising a high acid composition when using a pressure seal with or without heat. Without being bound by theory, it is believed that particles below 40% relative humidity on average are too brittle and obstruct the sealing process when compared to particles having a relative humidity greater than 40% that are able to more easily flow, are more pliable, and are able to release moisture during the bonding process. It has also been surprisingly found that, at a relative humidity greater than 70%, the acid particles, herein the form of citric acid, will agglomerate and form a paste that does not allow one to create a fibrous water-soluble unit dose having distinct active particles. Additionally, the agglomerated particles may impact the manufacturing equipment by adhering to the surface of the equipment.

Dependent upon the manufacturing choice of raw materials and settings, it has been found that one can increase or decrease the production of acetate. The acetate may create a desirable vinegar like scent from the fibrous water-soluble unit dose. The desirable vinegar like scent may be controlled by degree of hydrolysis of polyvinylalcohol made from polyvinylacetate, pH of the product during manufacture, product pH upon storage, incorporation of acetic acid and/or its salts, level of moisture incorporated into the product and ambient moisture of the product upon storage.

Particle-Fiber Layer

A particle-fiber layer may be arranged in several ways. Clusters of particles may be distributed in pockets distributed in the layer, where such pockets may be formed between layers of fibrous elements; the contact network and porosity within each cluster of particles is governed by physics of conventional particle packing, yet the clusters are substantially dilated in the layer. The particles may be distributed relatively homogeneously throughout the fibrous structure, substantially free of local particle clusters; packing is substantially dilated on the scale of individual particles, with fewer inter-particle contacts and greater inter-particle porosity. Without wishing to be bound by theory, it is believed that a fibrous water-soluble unit dose article comprising a layer comprising fibrous elements and particles, where sticky surfactants, such as AES, are segregated into particles having a dilated structure, provides for an improvement in dispersion and dissolution of the unit dose article, both by faster imbibition of water into the dilated structure and by a reduction in contacts among particles having sticky surfactants.

Pouches. The single unit dose may be in the form of a pouch. The composition may be provided in the form of a unitized dose, either tablet form or preferably in the form of a liquid/solid (optionally granules)/gel/paste held within a water-soluble film in what is known as a pouch or pod. The composition can be encapsulated in a single or multi-compartment pouch. Multi-compartment pouches are described in more detail in EP-A-2133410. Shading or non-shading dyes or pigments or other aesthetics may also be used in one or more compartments.

Suitable film for forming the pouches is soluble or dispersible in water, and preferably has a water-solubility/dispersibility of at least 50%, preferably at least 75% or even at least 95%, as measured by the method set out here after using a glass-filter with a maximum pore size of 20 microns:

50 grams±0.1 gram of pouch material is added in a pre-weighed 400 ml beaker and 245 ml±1 ml of distilled water is added. This is stirred vigorously on a magnetic stirrer set at 600 rpm, for 30 minutes. Then, the mixture is filtered through a folded qualitative sintered-glass filter with a pore size as defined above (max. 20 micron). The water is dried off from the collected filtrate by any conventional method, and the weight of the remaining material is determined (which is the dissolved or dispersed fraction). Then, the percentage solubility or dispersability can be calculated. Preferred film materials are polymeric materials. The film material can be obtained, for example, by casting, blow-moulding, extrusion or blown extrusion of the polymeric material, as known in the art. Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 to 1,000,000, more preferably from about 10,000 to 300,000 yet more preferably from about 20,000 to 150,000. Mixtures of polymers can also be used as the pouch material. This can be beneficial to control the mechanical and/or dissolution properties of the compartments or pouch, depending on the application thereof and the required needs. Suitable mixtures include for example mixtures wherein one polymer has a higher water-solubility than another polymer, and/or one polymer has a higher mechanical strength than another polymer. Also suitable are mixtures of polymers having different weight average molecular weights, for example a mixture of PVA or a copolymer thereof of a weight average molecular weight of about 10,000-40,000, preferably around 20,000, and of PVA or copolymer thereof, with a weight average molecular weight of about 100,000 to 300,000, preferably around 150,000. Also, suitable herein are polymer blend compositions, for example comprising hydrolytically degradable and water-soluble polymer blends such as polylactide and polyvinyl alcohol, obtained by mixing polylactide and polyvinyl alcohol, typically comprising about 1-35% by weight polylactide and about 65% to 99% by weight polyvinyl alcohol. Preferred for use herein are polymers which are from about 60% to about 98% hydrolysed, preferably about 80% to about 90% hydrolysed, to improve the dissolution characteristics of the material.

PVA used in the water soluble unit doses may be obtained from one or more suppliers, including but not limited to those obtained from Kuraray company limited (Tokyo, Japan) such as, for example, Poval 3-80, Poval 32-80, Poval 5-74, and Poval 10-78.

Naturally, different film material and/or films of different thickness may be employed in making the compartments. A benefit in selecting different films is that the resulting compartments may exhibit different solubility or release characteristics.

Most preferred film materials are PVA films known under the MonoSol trade reference M8630, M8900, H8779 (as described in the Applicants co-pending applications ref 44528 and 11599) and those described in U.S. Pat. Nos. 6,166,117 and 6,787,512 and PVA films of corresponding solubility and deformability characteristics.

The film material herein can also comprise one or more additive ingredients. For example, it can be beneficial to add plasticisers, for example glycerol, ethylene glycol, diethyleneglycol, propylene glycol, sorbitol and mixtures thereof. Other additives include functional detergent additives to be delivered to the wash water, for example organic polymeric dispersants, etc.

Bittering agent may be incorporated into a pouch or pod, either by incorporation in the composition inside the pouch, and/or by coating onto the film.

Method of Cleaning

The fibrous water-soluble unit dose may be used to clean one or more types of surfaces such as, for example without limitation, natural stones including but not limited to granite and marble, cement, concrete floors, concrete structures, porcelain, glass, metals, painted surfaces, plastics, and combinations thereof.

The fibrous water-soluble unit dose may be fully or partially dissolved in a given quantity of a dissolving fluid comprising water. More than one fibrous water-soluble unit dose may be dissolved in a given quantity of water. The dissolving fluid may comprise additional actives including but not limited to surfactants, salts, scrubbing agents, and enzymes. The dissolving fluid may be between 10% water and 100% water, such as, for example, between 30% water and 100% water, between 50% water and 100% water, and between 75% water and 100% water. The fibrous water-soluble unit does may be wetted by a dissolving fluid and used to clean a surface while in partially solid form.

The fibrous water-soluble unit dose may be added to a container that allows dissolving fluid to pass through the container, dissolving the fibrous water-soluble unit dose and incorporating it into the dissolving fluid that leaves the container.

The fibrous water-soluble unit dose may be added to a structure such as a sponge that allows it to slowly dissolve and/or combine with the dissolving fluid within its structure.

The dissolving fluid incorporation the fibrous water-soluble unit dose may be used to clean a chosen surface such as those described above.

The fibrous water-soluble unit dose may be used to clean one or more types of surfaces such as, for example without limitation, natural stones including but not limited to granite and marble, cement, concrete floors, concrete structures, porcelain, glass, metals, painted surfaces, plastics, and combinations thereof.

The fibrous water-soluble unit dose may be fully or partially dissolved in a given quantity of a dissolving fluid comprising water. More than one fibrous water-soluble unit dose may be dissolved in a given quantity of water. The dissolving fluid may comprise additional actives including but not limited to surfactants, salts, scrubbing agents, and enzymes. The dissolving fluid may be between 10% water and 100% water, such as, for example, between 30% water and 100% water, between 50% water and 100% water, and between 75% water and 100% water. The fibrous water-soluble unit does may be wetted by a dissolving fluid and used to clean a surface while in partially solid form.

The fibrous water-soluble unit dose may be added to a container that allows dissolving fluid to pass through the container, dissolving the fibrous water-soluble unit dose and incorporating it into the dissolving fluid that leaves the container.

The fibrous water-soluble unit dose may be added to a structure such as a sponge that allows it to slowly dissolve and/or combine with the dissolving fluid within its structure.

The dissolving fluid incorporation the fibrous water-soluble unit dose may be used to clean a chosen surface such as those described above.

In one aspect, the present invention encompasses a method of cleaning a toilet bowl of a toilet comprising the steps of: adding a fibrous water-soluble unit dose article to said toilet bowl containing water; allowing said article to distintegrate in said water; and flushing said toilet after a period of at least 5 minutes, preferably at least 30 minutes, preferably at least 60 minutes, preferably at least 180 minutes, from said article being added to said water of said toilet bowl.

In one aspect, the present invention encompasses a method of cleaning a surface comprising the steps of: providing a vessel containing water; adding a fibrous water-soluble unit dose article to said vessel containing water; allowing said article to disintegrate in said water to form a cleaning solution; and contacting said surface with said cleaning solution. Preferably the vessel is a bucket or a household sink. Preferably the surface is selected from the group consisting of household hard surfaces, exterior car surfaces, and dishware but may include any of the surfaces disclosed above.

In one aspect, the present invention encompasses a method of cleaning a washing vessel such as a washing machine, dishwasher, or bathtub, the method comprising of providing a vessel containing water; adding a fibrous water-soluble unit dose article to said vessel containing water; allowing said article to disintegrate in said water to form a cleaning solution; and contacting said surface with said cleaning solution. Preferably the vessel is a washing machine, dishwasher, or bathtub.

In one aspect, the present invention encompasses a method of cleaning a garbage disposal comprising of providing a vessel containing water; adding a fibrous water-soluble unit dose article to said vessel containing water; allowing said article to disintegrate in said water to form a cleaning solution; and pouring the cleaning solution into the garbage disposal. The garbage disposal may either be in the on or in the off cycle.

Method of Laundering

The present invention also encompasses a method of laundering using a fibrous water-soluble unit dose, comprising the steps of, placing at least one fibrous water-soluble unit dose into the washing machine along with the laundry to be washed, and carrying out a washing or cleaning operation. Specifically, the method may include obtaining a fabric, treating the fabric in a wash step, wherein the wash step includes contacting the fabric with a wash liquor. Wherein the wash liquor is prepared by diluting a fibrous water-soluble unit dose and a detergent dose in water by between 300 and 800 fold, preferably between 400 and 700 fold; wherein the wash liquor consists of a pH less than or equal to 6.

Additionally, the fibrous water-soluble unit dose may be added to a rinse cycle or in the rinse cycle container, alone or in combination with an additional rinse agent, such that the rinse liquor consists of a pH of less than or equal to 6.

Any suitable washing machine may be used. Examples include an automatic washing machine, a manual wash operation or a mixture thereof, preferably an automatic washing machine. Those skilled in the art will recognize suitable machines for the relevant wash operation.

The fibrous water-soluble unit dose may be used in combination with other compositions, such as fabric additives, fabric softeners, rinse aids and the like.

The wash temperature may be between 5° C. and 90° C., such as, for example, 30° C. or less. The wash process may comprise at least one wash cycle having a duration of between 5 and 50 minutes. The automatic laundry machine may comprise a rotating drum, and wherein during at least one wash cycle, the drum has a rotational speed of between 15 and 40 rpm, preferably between 20 and 35 rpm.

The fabric may be cotton, polyester, cotton/polyester blends or a mixture thereof, preferably cotton.

Determination of pH

Unless otherwise stated herein, the pH of the composition is defined as the neat pH of the composition at 20±2° C. Any meter capable of measuring pH to ±0.01 pH units is suitable. Orion meters (Thermo Scientific, Clintinpark—Keppekouter, Ninovesteenweg 198, 9320 Erembodegem—Aalst, Belgium) or equivalent are acceptable instruments. The pH meter should be equipped with a suitable glass electrode with calomel or silver/silver chloride reference. An example includes Mettler DB 115. The electrode should be stored in the manufacturer's recommended electrolyte solution. The pH is measured according to the standard procedure of the pH meter manufacturer. Furthermore, the manufacturer's instructions to set up and calibrate the pH assembly should be followed.

Basis Weight Test Method

Basis weight of a fibrous structure is measured on stacks of twelve usable units using a top loading analytical balance with a resolution of ±0.001 g. The balance is protected from air drafts and other disturbances using a draft shield. A precision cutting die, measuring 3.500 in ±0.0035 in by 3.500 in ±0.0035 in is used to prepare all samples.

With a precision cutting die, cut the samples into squares. Combine the cut squares to form a stack twelve samples thick. Measure the mass of the sample stack and record the result to the nearest 0.001 g.

The Basis Weight is calculated in lbs/3000 ft$^2$ or g/m$^2$ as follows:

Basis Weight=(Mass of stack)/[(Area of 1 square in stack)×(No. of squares in stack)]

For example,

Basis Weight (lbs/3000 ft$^2$)=[[Mass of stack (g)/453.6 (g/lbs)]/[12.25 (in$^2$)/144 (in$^2$/ft$^2$)×12]]×3000 or,

Basis Weight (g/m$^2$)=Mass of stack (g)/[79.032 (cm$^2$)/10,000 (cm$^2$/m$^2$)×12]

Report result to the nearest 0.1 lbs/3000 ft$^2$ or 0.1 g/m$^2$. Sample dimensions can be changed or varied using a similar precision cutter as mentioned above, so as at least 100 square inches of sample area in stack.

EXAMPLES

Example 1

| Raw Material | Citrocoat Particle (%) | Web (%) | Finished Pad (g) | Finished Pad (%) |
|---|---|---|---|---|
| NaAS (from fiber) | 0.00% | 21.56% | 0.80 | 6.63% |
| NaLAS (from fiber & particle) | 0.00% | 43.11% | 1.60 | 13.26% |
| Citrocoat (from particle) | 100.00% | 0.00% | 8.38 | 69.23% |
| PVOH 505 (from fiber) | 0.00% | 29.33% | 1.09 | 9.03% |
| PEOn10 (from fiber) | 0.00% | 2.60% | 0.10 | 0.80% |
| PEOn60k (from fiber) | 0.00% | 0.40% | 0.01 | 0.12% |
| Misc & Moisture | 0.00% | 3.00% | 0.11 | 0.92% |
| Web TOTAL | 100.00% | 100.00% | 12.10 | 100.00% |
| Charm TOTAL | | | 12.10 | 100.00% |
| Pad/Dose | | | | 1.00 |
| Surfactant/Dose (g) | | | | 2.41 |
| PVOH/Dose (g) | | | | 1.20 |
| Dose Wt | | | | 12.10 |
| % LAS | | | | 67% |

-continued

| Raw Material | Citrocoat Particle (%) | Web (%) | Finished Pad (g) | Finished Pad (%) |
|---|---|---|---|---|
| 6" × 1 m Weight (g) (193 OK) | | | 130 | |
| Total Product Basis Wt (GSM) (ET4 = 3333) | | | 2574 | |

Raw Materials for Examples

LAS is linear alkylbenzenesulfonate having an average aliphatic carbon chain length $C_{11}$-$C_{12}$ supplied by Stepan, Northfield, Illinois, USA or Huntsman Corp. HLAS is acid form.

AS is a $C_{12-14}$ sulfate, supplied by Stepan, Northfield, Illinois, USA, and/or a mid-branched alkyl sulfate.

PEG-PVAc polymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany)

Ethoxylated Polyethylenimine (PE20) is a 600 g/mol molecular weight polyethylenimine core with 20 ethoxylate groups per —NH. Available from BASF (Ludwigshafen, Germany).

Citrocoat (NF5000) is available from Jungbunzlauer (Basel, Switzerland).

PVOH and Celvol® are available from Sekisui Specialty Chemicals America, LLC located in Dallas Texas Example 2

| Raw Material | Citrocoat Particle (%) | PVA Web (%) | Finished Pad (g) | Finished Pad (%) |
|---|---|---|---|---|
| Celvol ® 523 | 0.00% | 32.00% | 1.20 | 9.89 |
| Celvol ® 205 | 0.00% | 32.00% | 1.20 | 9.89 |
| Sorbitol | 0.00% | 32.00% | 1.20 | 9.89 |
| Citrocoat (from particle) | 100.00% | 0.00% | 8.40 | 69.14% |
| Misc & Moisture | 0.00% | 4.00% | 0.15 | 1.19% |
| Web TOTAL | 100.00% | 100.00% | 12.15 | 100.00% |
| Pad TOTAL | | | 12.15 | 100.00% |
| Pad/Dose | | | 1.00 | |
| PVOH/Dose (g) | | | 3.60 | |
| Dose Wt | | | 12.15 | |
| 6" × 1 m Weight (g) (193 OK) | | | 130 | |
| Total Product Basis Wt (GSM) (ET4 = 3333) | | | 2570 | |

The formulas described above may be used to deliver a consumer desirable vinegar scent without the inclusion of vinegar. This desirable scent is delivered by the presence of acetic acid. The acetic acid concentration may be in the parts per million, such as between 1 part per million and 10,000 parts per million, provided that is present. The presence of acetic acid allows for the product to deliver a desirable scent to the consumer when they open the package containing the water-soluble article. Without being bound by theory, the desirable vinegar like scent may be controlled by degree of hydrolysis of polyvinyl alcohol made from polyvinyl acetate, pH of the product during manufacture, product pH upon storage, incorporation of acetic acid and/or its salts, level of moisture incorporated into the product and ambient moisture of the product upon storage. Additionally, without being bound by theory, one may increase or reduce the presence of acetic acid and therefore the level of vinegar odor by manipulating the formulation to increase or reduce the polymer. For example, a fibrous structure comprising of starch may not produce acetic acid.

Figure 7:
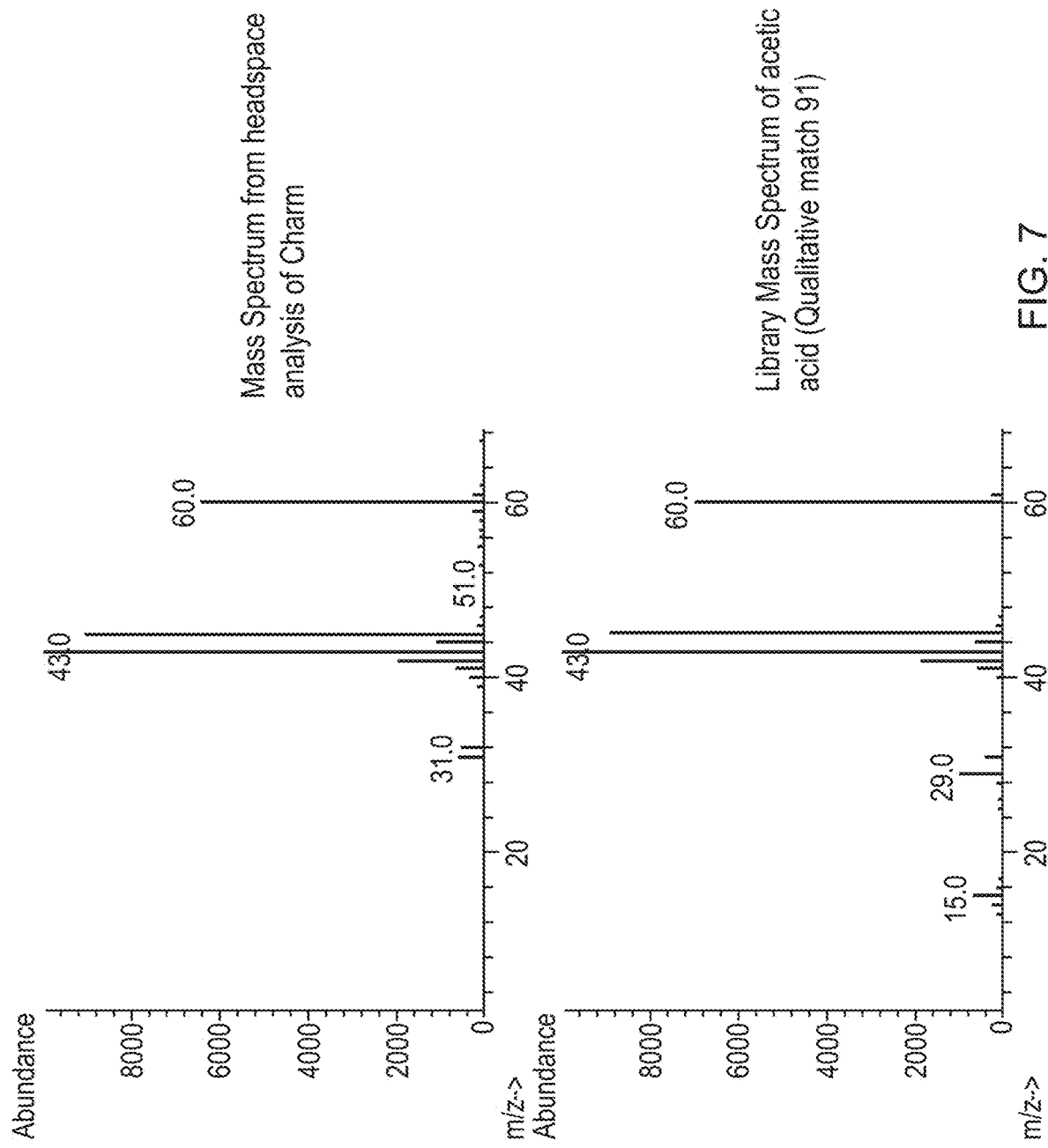
FIG. 7 is a mass spectrum analysis.

As shown in FIG. 7, the presence of acetic acid has been confirmed using mass spectrometry measuring the headspace of the water-soluble article of Example 1 in comparison to the mass spectrometry standard for acetic acid.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

For clarity purposes, the total "% wt" values do not exceed 100% wt.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples and/or embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fibrous water-soluble unit dose comprising:
    a soluble fibrous structure encasing an active agent, wherein said active agent comprises from 5% to 90% of an active agent acid, wherein the active agent acid has a coating comprising citrate.

2. The fibrous water-soluble unit dose of claim 1, wherein said active agent acid is selected from the group consisting acetic acid, adipic acid, aspartic acid, carboxymethyloxymalonic acid, carboxymethyloxysuccinic acid, citric acid, formic acid, glutaric acid, gluconic acid, hydroxyethyliminodiacetic acid, iminodiacetic acid, lactic acid, maleic acid, malic acid, malonic acid, oxydiacetic acid, oxydisuccinic acid, succinic acid, sulfamic acid, tartaric acid, tartaricdisuccinic acid, tartaric-monosuccinic acid, their salts or mixtures thereof, either alone or in combination.

3. The fibrous water-soluble unit dose of claim 1, wherein the active agent acid is comprises citric acid.

4. The fibrous water-soluble unit dose of claim 3, wherein the citric acid serves as a bittering agent within the fibrous water-soluble unit dose article.

5. The fibrous water-soluble unit dose article of claim 1, wherein the article comprises a bittering agent on an outer surface.

6. The fibrous water-soluble unit dose of claim 1, wherein the active agent comprises from about 50% to 70% by weight of the fibrous water-soluble unit dose.

7. The fibrous water-soluble unit dose of claim 1, wherein said soluble fibrous structure forms a pouch which encases said active agent.

8. The fibrous water-soluble unit dose of claim 1, wherein said active agent is commingled with said soluble fibrous structure to form a coform structure.

9. The fibrous water-soluble unit dose of claim 1, wherein said soluble fibrous structure comprises fibrous elements having a surfactant therein.

10. The fibrous water-soluble unit dose of claim 1, wherein the composition of the water-soluble article comprises of 50% or greater of bio-based materials.

11. The fibrous water-soluble unit dose of claim 1, wherein the fibrous structure comprises fibrous elements comprising starch.

12. The fibrous water-soluble unit dose of claim 1, wherein the fibrous water-soluble unit dose comprises acetic acid.

13. The fibrous water-soluble unit dose of claim 1, wherein the unit dose comprises an outer surface, wherein the outer surface comprises print.

\* \* \* \* \*